United States Patent
Blacker et al.

(10) Patent No.: US 9,649,455 B2
(45) Date of Patent: May 16, 2017

(54) INDICATING DEVICE

(71) Applicant: TRUDELL MEDICAL INTERNATIONAL, London (CA)

(72) Inventors: Richard Blacker, Surrey (CA); Daniel K. Engelbreth, London (CA); James N. Schmidt, London (CA)

(73) Assignee: Trudell Medical International, London (CA)

( * ) Notice: Subject to any disclaimer, the term of this patent is extended or adjusted under 35 U.S.C. 154(b) by 0 days.

(21) Appl. No.: 14/596,954

(22) Filed: Jan. 14, 2015

(65) Prior Publication Data

US 2015/0320946 A1 Nov. 12, 2015

Related U.S. Application Data

(60) Continuation of application No. 13/938,009, filed on Jul. 9, 2013, now Pat. No. 8,944,285, which is a
(Continued)

(51) Int. Cl.
*B67D 7/22* (2010.01)
*A61M 15/00* (2006.01)
(Continued)

(52) U.S. Cl.
CPC ...... *A61M 15/0071* (2014.02); *A61M 15/009* (2013.01); *A61M 15/0021* (2014.02);
(Continued)

(58) Field of Classification Search
CPC ............ A61M 15/009; A61M 15/0071; A61M 15/0021; A61M 15/007; A61M 15/0076;
(Continued)

(56) References Cited

U.S. PATENT DOCUMENTS 165,054 A  6/1875  Baldwin
498,851 A  6/1893  Jones
(Continued)

FOREIGN PATENT DOCUMENTS

AU      598250 B2   6/1990
CA    0 535 518 A   1/1957
(Continued)

OTHER PUBLICATIONS

U.S. Department of Health and Human Services, Food and Drug Administration, Center for Drug Evaluation and Research (CDER)—Clinical, "Guidance for Industry: Integration of Dose-Counting Mechanisms into MDI Drug Products-Draft Guidance," dated Nov. 2001, 6 pages.
(Continued)

*Primary Examiner* — Lien Ngo
(74) *Attorney, Agent, or Firm* — Brinks Gilson & Lione

(57) ABSTRACT

An indicating device for a dispenser that dispenses metered dosages of a medicament from a container having a valve moveable between a closed position and an open position. The indicating device includes an indicator housing having a first cover with a first vertical wall and a second cover with a second vertical wall. One of the first or second covers includes a base defining a lower surface of the indicator housing, and the other of the first or second covers includes a top defining an upper surface of the indicator housing. The first and second covers are joined with the first and second vertical walls and the base and the top defining an interior space therebetween. An indicator is rotatably disposed in the interior space of the indicator housing, with the indicator including dosage indicia. A dispensing device includes a dispenser housing and an indicating device.

15 Claims, 14 Drawing Sheets

Related U.S. Application Data continuation of application No. 13/431,237, filed on Mar. 27, 2012, now Pat. No. 8,505,773, which is a continuation of application No. 13/167,441, filed on Jun. 23, 2011, now Pat. No. 8,157,128, which is a continuation of application No. 12/454,564, filed on May 19, 2009, now Pat. No. 7,984,826, which is a continuation of application No. 11/287,818, filed on Nov. 28, 2005, now Pat. No. 7,575,130, which is a continuation of application No. 10/865,531, filed on Jun. 10, 2004, now Pat. No. 6,997,349, which is a continuation of application No. 10/369,091, filed on Feb. 18, 2003, now Pat. No. 6,938,796, which is a continuation of application No. 10/193,508, filed on Jul. 11, 2002, now Pat. No. 6,561,384, which is a continuation of application No. 09/954,428, filed on Sep. 14, 2001, now Pat. No. 6,435,372, which is a continuation of application No. 09/704,959, filed on Nov. 2, 2000, now abandoned, which is a division of application No. 09/149,708, filed on Sep. 8, 1998, now Pat. No. 6,161,724, which is a continuation-in-part of application No. 09/008,184, filed on Jan. 16, 1998, now Pat. No. 6,142,339.

(51) Int. Cl.
   *G06M 1/04* (2006.01)
   *G06M 1/08* (2006.01)
   *G06M 1/16* (2006.01)

(52) U.S. Cl.
   CPC .... *A61M 15/0065* (2013.01); *A61M 15/0068* (2014.02); *A61M 15/0075* (2014.02); *A61M 15/0076* (2014.02); *A61M 15/0081* (2014.02); *G06M 1/041* (2013.01); *G06M 1/083* (2013.01); *G06M 1/163* (2013.01)

(58) Field of Classification Search
   CPC .......... A61M 15/0073; A61M 15/0081; A61M 15/0068; A61M 15/0075; A61M 15/0065; B65D 83/52; G06M 1/041; G06M 1/083; G06M 1/163
   USPC ....... 222/36–38, 48, 23; 128/200.23, 205.23, 128/203.15
   See application file for complete search history.

(56) References Cited

U.S. PATENT DOCUMENTS

| | | |
|---|---|---|
| 1,219,858 A | 3/1917 | Patterson |
| 2,455,962 A | 12/1948 | Wheeler et al. |
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,074,831 A | 2/1978 | Roach |
| 4,078,661 A | 3/1978 | Thomas |
| 4,094,408 A | 6/1978 | Ford |
| 4,117,952 A | 10/1978 | Grimes |
| 4,162,746 A | 7/1979 | Anderson et al. |
| 4,164,301 A | 8/1979 | Thayer |
| 4,171,753 A | 10/1979 | Vreede |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |

(56) References Cited

U.S. PATENT DOCUMENTS

| | | |
|---|---|---|
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 2,841,190 A | 7/1987 | Sheck |
| 4,677,975 A | 7/1987 | Edgar et al. |
| 4,693,399 A | 9/1987 | Hickman et al. |
| 4,705,182 A | 11/1987 | Newel-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,860,740 A | 8/1989 | Kirk et al. |
| 4,890,572 A | 1/1990 | Huang |
| 4,934,358 A | 6/1990 | Nilsson et al. |
| 4,934,568 A | 6/1990 | Fuchs |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,056,454 A | 10/1991 | Turner |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,226,539 A | 7/1993 | Cheng |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Ambrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |
| 5,331,953 A | 7/1994 | Andersson et al. |
| 5,335,823 A | 8/1994 | Fuchs et al. |
| 5,349,944 A | 9/1994 | Chippendale et al. |
| 5,349,945 A | 9/1994 | Wass et al. |
| 5,356,012 A | 10/1994 | Tang et al. |
| 5,356,406 A | 10/1994 | Schraga |
| 5,363,842 A | 11/1994 | Mishelevich et al. |
| 5,370,267 A | 12/1994 | Schroeder |
| 5,378,233 A | 1/1995 | Haber et al. |
| 5,379,804 A | 1/1995 | Dunn et al. |
| 5,382,243 A | 1/1995 | Mulholland |
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |
| 5,421,482 A | 6/1995 | Garby et al. |
| 5,437,270 A | 8/1995 | Braithwaite |
| 5,447,150 A | 9/1995 | Bacon |
| 5,448,042 A | 9/1995 | Robinson et al. |
| 5,468,233 A | 11/1995 | Schraga |
| 5,482,030 A | 1/1996 | Klein |
| 5,482,163 A | 1/1996 | Hoffman |
| 5,498,243 A | 3/1996 | Vallelunga et al. |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,524,613 A | 6/1996 | Haber et al. |
| 5,544,647 A | 8/1996 | Jewett et al. |
| 5,549,101 A | 8/1996 | Trofast et al. |
| 5,564,414 A * | 10/1996 | Walker .............. A61M 15/0065 128/200.23 |
| 5,574,268 A | 11/1996 | Herman et al. |
| 5,577,335 A | 11/1996 | Tucker |
| 5,584,815 A | 12/1996 | Pawelka et al. |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,626,566 A | 5/1997 | Petersen et al. |
| 5,638,970 A | 6/1997 | Garby et al. |
| 5,657,748 A | 8/1997 | Braithwaite |
| 5,676,129 A | 10/1997 | Rocci, Jr. et al. |
| 5,687,710 A | 11/1997 | Ambrosio et al. |
| 5,692,492 A | 12/1997 | Bruna et al. |
| 5,694,882 A | 12/1997 | Marshall |
| 5,697,916 A | 12/1997 | Schraga |
| 5,718,355 A * | 2/1998 | Garby ...................... A61J 7/04 116/285 |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A * | 9/1998 | Wolf .................. A61M 15/009 128/200.23 |
| 5,826,571 A | 10/1998 | Casper et al. |
| 5,829,434 A | 11/1998 | Ambrosio et al. |
| 5,845,777 A | 12/1998 | Najmi |
| 5,852,590 A | 12/1998 | De La Huerga |
| 5,871,007 A | 2/1999 | Clark, Jr. |
| 5,873,995 A | 2/1999 | Huang et al. |
| 5,882,507 A | 3/1999 | Tanner et al. |
| 5,896,855 A | 4/1999 | Hobbs |
| 5,896,990 A | 4/1999 | Barzana |
| 5,899,201 A | 5/1999 | Schultz et al. |
| 5,904,139 A | 5/1999 | Hauser |
| 5,957,896 A | 9/1999 | Bendek et al. |
| 5,961,495 A | 10/1999 | Walters et al. |
| 5,988,496 A | 11/1999 | Bruna |
| 6,000,159 A | 12/1999 | Hornung |
| 6,001,082 A | 12/1999 | Dair et al. |
| 6,012,450 A | 1/2000 | Rubsamen |
| 6,029,659 A * | 2/2000 | O'Connor ............ A61M 15/009 128/200.23 |
| 6,059,133 A | 5/2000 | Lai |
| 6,062,214 A | 5/2000 | Howlett |
| 6,076,521 A | 6/2000 | Lindahl et al. |
| 6,082,358 A | 7/2000 | Scarrott et al. |
| 6,089,180 A | 7/2000 | Nichols, Jr. |

(56) References Cited

U.S. PATENT DOCUMENTS

| | | |
|---|---|---|
| 6,096,010 A | 8/2000 | Walters et al. |
| 6,119,684 A | 9/2000 | Nohl et al. |
| 6,138,669 A | 10/2000 | Rocci, Jr. et al. |
| 6,142,339 A | 11/2000 | Blacker et al. |
| 6,148,815 A | 11/2000 | Wolf |
| 6,149,054 A | 11/2000 | Cirrillo |
| 6,155,251 A | 12/2000 | Hauser |
| 6,161,724 A | 12/2000 | Blacker et al. |
| 6,164,494 A | 12/2000 | Marelli |
| 6,182,655 B1 | 2/2001 | Keller et al. |
| 6,186,364 B1 | 2/2001 | Dobbs |
| 6,202,642 B1 | 3/2001 | McKinnon et al. |
| 6,221,053 B1 | 4/2001 | Walters et al. |
| 6,223,744 B1 | 5/2001 | Garon |
| 6,234,168 B1 | 5/2001 | Bruna |
| 6,283,365 B1 | 9/2001 | Bason |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,405,727 B1 | 6/2002 | MacMichael et al. |
| 6,415,785 B1 | 7/2002 | Stage |
| 6,425,392 B1 | 7/2002 | Sosiak |
| 6,431,168 B1 | 8/2002 | Rand et al. |
| 6,435,372 B1 | 8/2002 | Blacker et al. |
| 6,446,627 B1 | 9/2002 | Bowman et al. |
| 6,474,331 B1 | 11/2002 | Rand et al. |
| 6,481,438 B1 | 11/2002 | Gallem et al. |
| 6,484,717 B1 | 11/2002 | Dagsland et al. |
| 6,516,799 B1 | 2/2003 | Greenwood et al. |
| 6,529,446 B1 | 3/2003 | De La Huerga |
| 6,561,384 B2 | 5/2003 | Blacker et al. |
| 6,601,582 B2 | 8/2003 | Rand et al. |
| 6,615,827 B2 | 9/2003 | Greenwood et al. |
| 6,659,307 B1 | 12/2003 | Stradella |
| 6,679,251 B1 | 1/2004 | Gallem et al. |
| 6,701,917 B2 | 3/2004 | O'Leary |
| 6,718,972 B2 | 4/2004 | O'Leary |
| 6,729,330 B2 | 5/2004 | Scarrott et al. |
| 6,752,153 B1 | 6/2004 | Eckert |
| 6,761,161 B2 | 7/2004 | Scarrott et al. |
| 6,766,799 B2 | 7/2004 | Edwards et al. |
| 6,769,601 B2 | 8/2004 | Haikarainen et al. |
| 6,907,876 B1 | 6/2005 | Clark et al. |
| 6,938,796 B2 | 9/2005 | Blacker et al. |
| 6,997,349 B2 | 2/2006 | Blacker et al. |
| 7,137,391 B2 | 11/2006 | Bruna |
| 7,143,764 B1 | 12/2006 | Dagsland et al. |
| 7,143,908 B2 | 12/2006 | Blacker et al. |
| 7,156,258 B2 | 1/2007 | Eckert |
| 7,407,066 B2 | 8/2008 | Ouyang et al. |
| 7,555,995 B1 | 7/2009 | Stump et al. |
| 7,575,130 B2 | 8/2009 | Blacker et al. |
| 7,743,945 B2 | 6/2010 | Lu et al. |
| 7,793,798 B2 | 9/2010 | Stradella et al. |
| 7,886,934 B2 | 2/2011 | Lu et al. |
| 7,984,826 B2 | 7/2011 | Blacker et al. |
| 8,082,873 B2 | 12/2011 | Nuttall |
| 8,157,128 B2 | 4/2012 | Blacker et al. |
| 8,505,773 B2 | 8/2013 | Blacker et al. |
| 2002/0000225 A1 | 1/2002 | Schuler et al. |
| 2002/0153005 A1 | 10/2002 | Scarrott et al. |
| 2003/0183225 A1 | 10/2003 | Knudsen |
| 2003/0200964 A1 | 10/2003 | Blakley et al. |
| 2003/0205227 A1 | 11/2003 | Hodson |
| 2003/0209239 A1 | 11/2003 | Rand et al. |
| 2004/0065326 A1 | 4/2004 | MacMichael et al. |
| 2004/0069301 A1 | 4/2004 | Bacon |
| 2004/0094147 A1 | 5/2004 | Schyra et al. |
| 2004/0144798 A1 | 7/2004 | Ouyang et al. |
| 2004/0149772 A1 | 8/2004 | Ouyang |
| 2004/0149773 A1 | 8/2004 | Ouyang et al. |
| 2004/0221840 A1 | 11/2004 | Stockman-Lamb |
| 2004/0255935 A1 | 12/2004 | Bruna |
| 2004/0255936 A1 | 12/2004 | Urbanus |
| 2005/0011515 A1 | 1/2005 | Lee et al. |
| 2005/0056276 A1 | 3/2005 | Schuler et al. |
| 2005/0268905 A1 | 12/2005 | Rasmussen et al. |
| 2005/0284471 A1 | 12/2005 | Bruna |
| 2006/0254581 A1 | 11/2006 | Genova et al. |
| 2007/0084462 A1 | 4/2007 | Allen |
| 2010/0078490 A1* | 4/2010 | Fenlon ................ A61M 15/009 235/91 R |

FOREIGN PATENT DOCUMENTS

| | | |
|---|---|---|
| CA | 2 093 809 A1 | 2/1993 |
| CA | 2 152 088 A | 7/1994 |
| CA | 2 181 789 C | 6/1996 |
| CA | 2 486 892 A1 | 12/1998 |
| CA | 2 315 777 A1 | 7/1999 |
| CA | 2 331 179 A1 | 11/1999 |
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| DE | 6 603 758 U | 10/1969 |
| DE | 27 02 539 A1 | 1/1977 |
| DE | 33 36 486 A1 | 4/1984 |
| DE | 86 02 238 U1 | 4/1986 |
| DE | 85 90 143 U1 | 4/1987 |
| EP | 0 028 929 A2 | 5/1981 |
| EP | 0 098 939 A2 | 1/1984 |
| EP | 0 114 617 A2 | 8/1984 |
| EP | 0 063 599 A1 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 949 584 A2 | 10/1999 |
| EP | 1 369 139 A1 | 12/2003 |
| EP | 1 220 802 B1 | 2/2004 |
| FR | 2 743 055 A1 | 7/1997 |
| GB | 0 998 148 A | 7/1965 |
| GB | 1 058 636 A | 2/1967 |
| GB | 1 290 484 A | 9/1972 |
| GB | 1 317 315 A | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| GB | 2 414 187 A | 11/2005 |
| JP | 61-55759 A | 4/1986 |
| JP | 62-121670 U | 8/1987 |
| JP | 04-50059 A | 4/1992 |
| JP | 06-26891 A | 4/1994 |
| WO | WO 86/02275 A1 | 4/1986 |
| WO | WO 87/04354 A1 | 8/1987 |
| WO | WO 90/10470 A1 | 9/1990 |
| WO | WO 91/06334 A1 | 5/1991 |
| WO | WO 92/07600 A1 | 5/1992 |
| WO | WO 92/09324 A1 | 6/1992 |
| WO | WO 92/15353 A2 | 9/1992 |
| WO | WO 92/17231 A1 | 10/1992 |
| WO | WO 93/24167 A1 | 12/1993 |
| WO | WO 94/11272 A1 | 5/1994 |
| WO | WO 94/14492 A2 | 7/1994 |
| WO | WO 95/34874 A1 | 12/1995 |
| WO | WO 96/16686 A1 | 6/1996 |
| WO | WO 96/16687 A1 | 6/1996 |
| WO | WO 96/39337 A1 | 12/1996 |
| WO | WO 98/01822 A1 | 1/1998 |
| WO | WO 98/56444 A1 | 12/1998 |
| WO | WO 98/56445 A1 | 12/1998 |
| WO | WO 99/36115 A2 | 7/1999 |
| WO | WO 99/57019 A2 | 11/1999 |
| WO | WO 00/09187 A1 | 2/2000 |
| WO | WO 00/59806 A1 | 10/2000 |
| WO | WO 01/28887 A1 | 4/2001 |
| WO | WO 01/29765 A1 | 4/2001 |

(56) References Cited

FOREIGN PATENT DOCUMENTS

| WO | WO 01/37909 A1 | 5/2001 |
| WO | WO 03/101514 A1 | 12/2003 |
| WO | WO 03/103759 A1 | 12/2003 |
| WO | WO 2004/089451 A1 | 10/2004 |
| WO | WO 2006/110080 A1 | 10/2006 |

OTHER PUBLICATIONS

English language translation of Office Action for Japanese Application No. 2008-019458 dispatched Sep. 29, 2009, 2 pages.
Office Action, and English language translation thereof, from counterpart Japanese Application No. 2008-189362, dated Jun. 14, 2011, 4 pages.

* cited by examiner

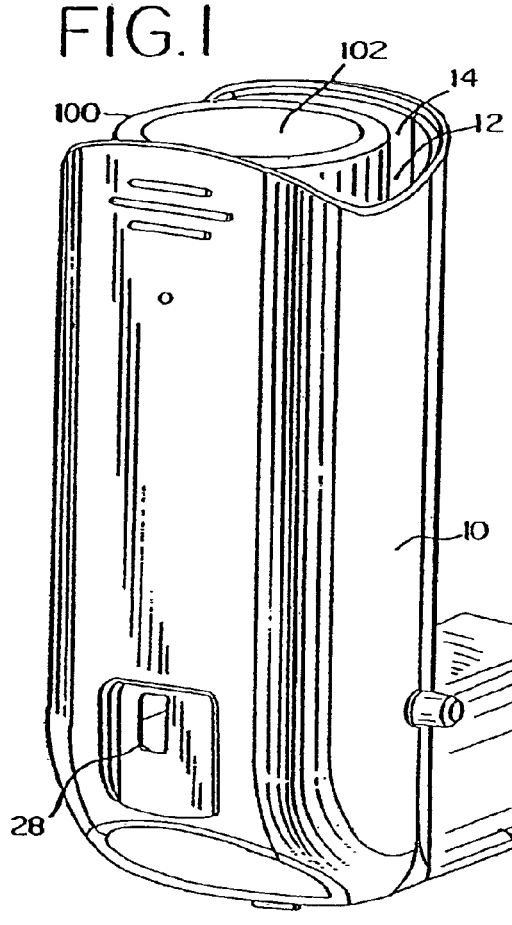
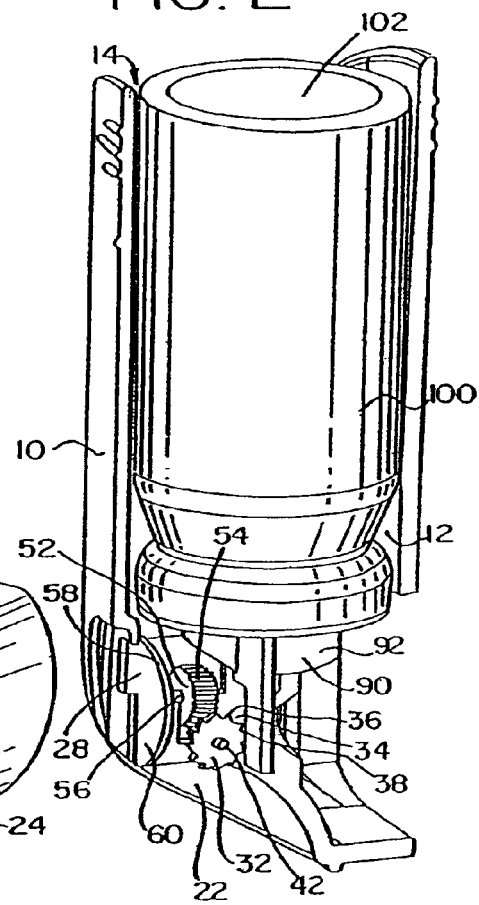
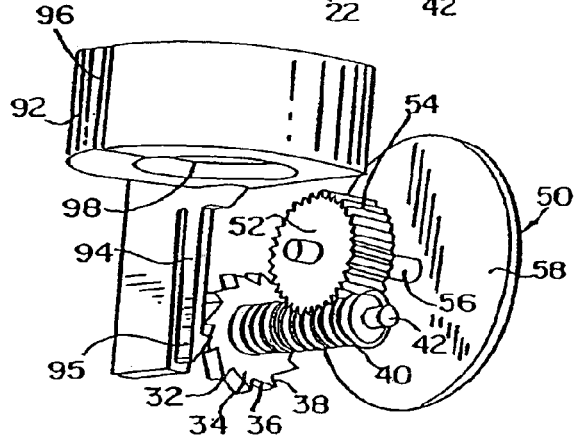

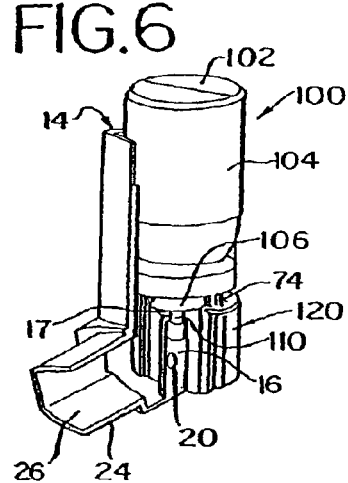
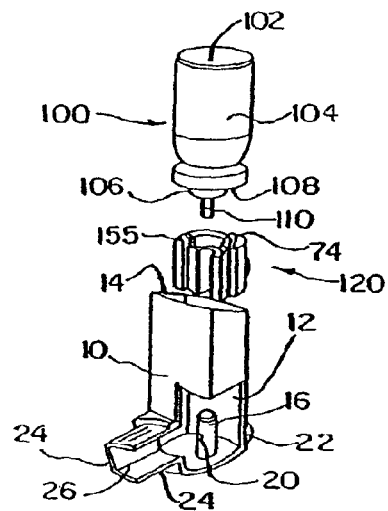
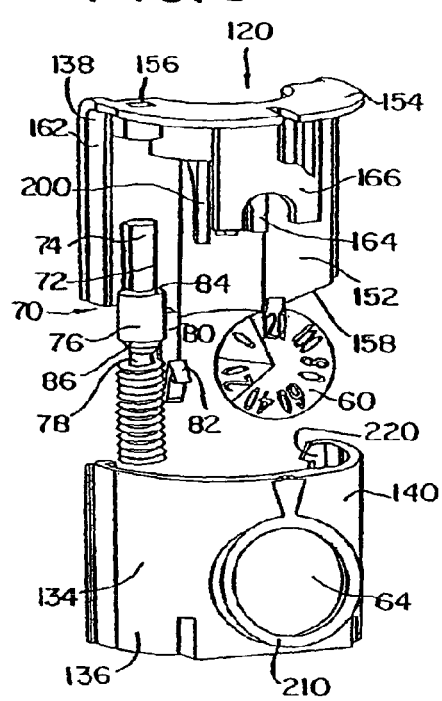
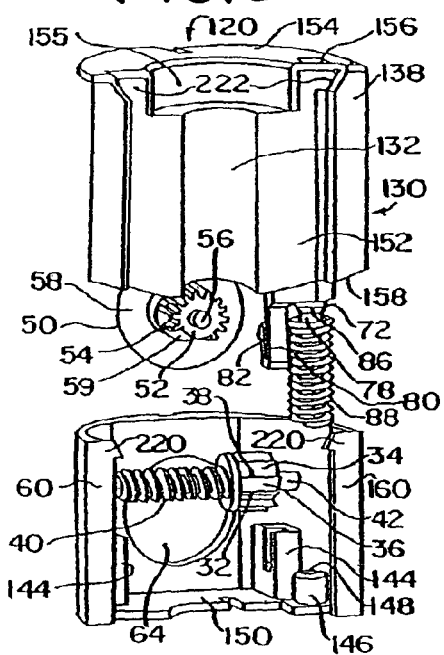

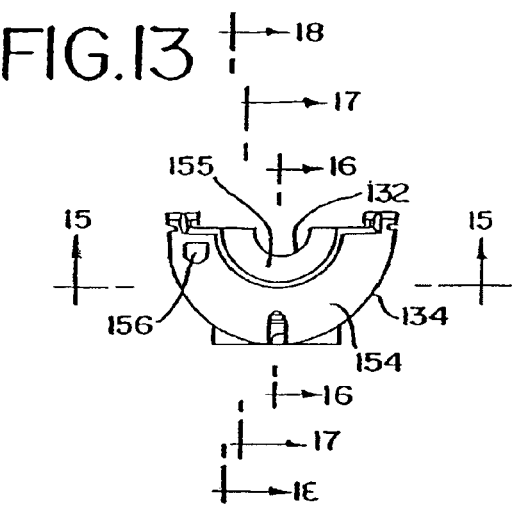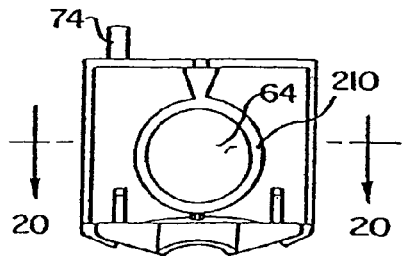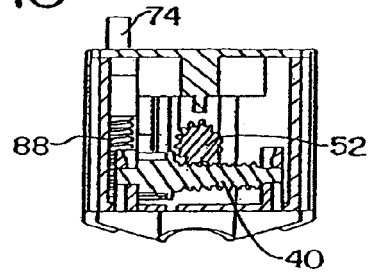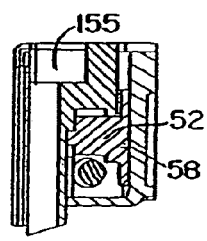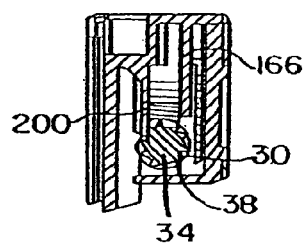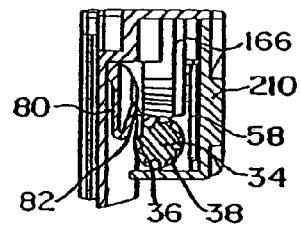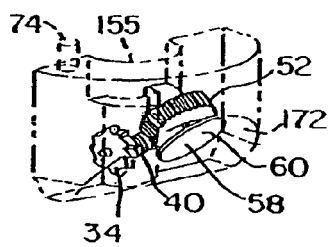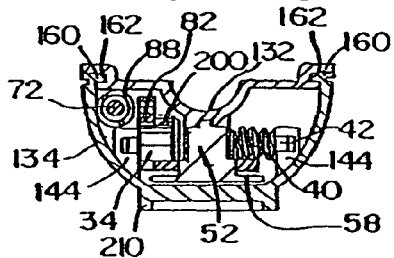

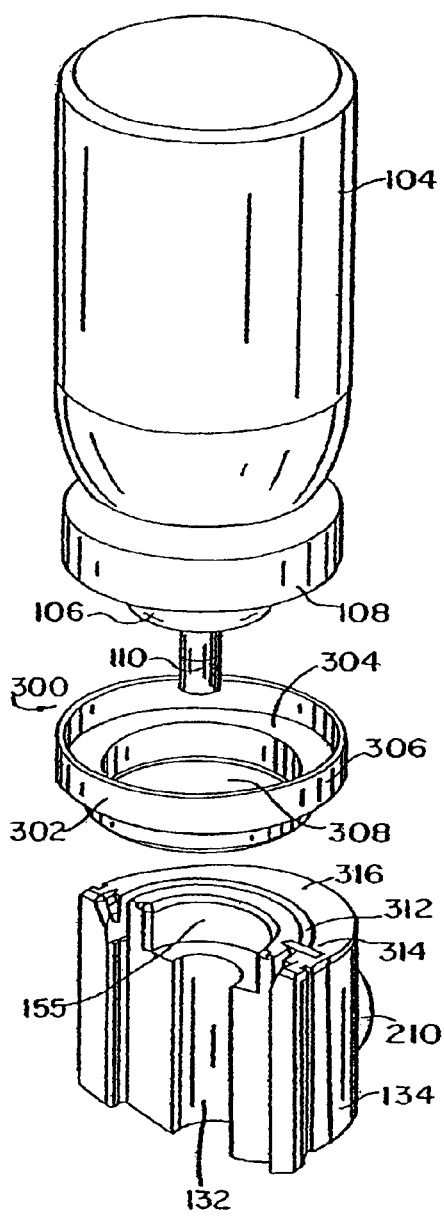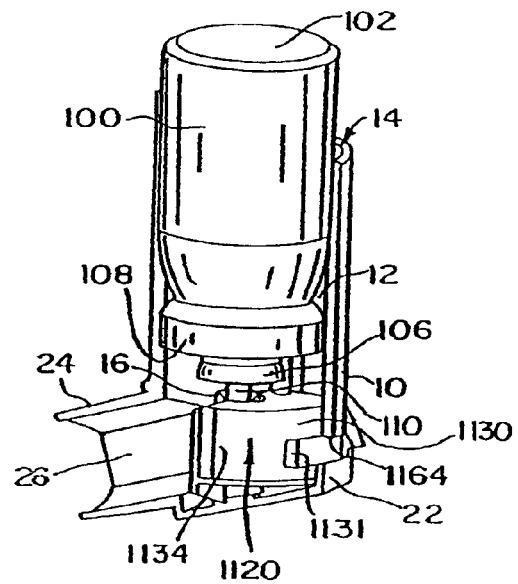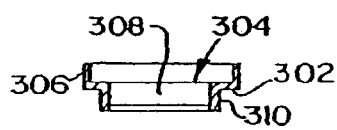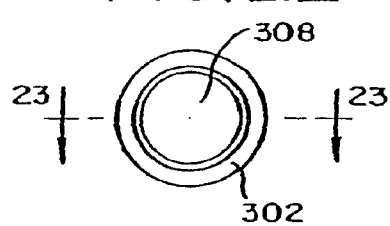

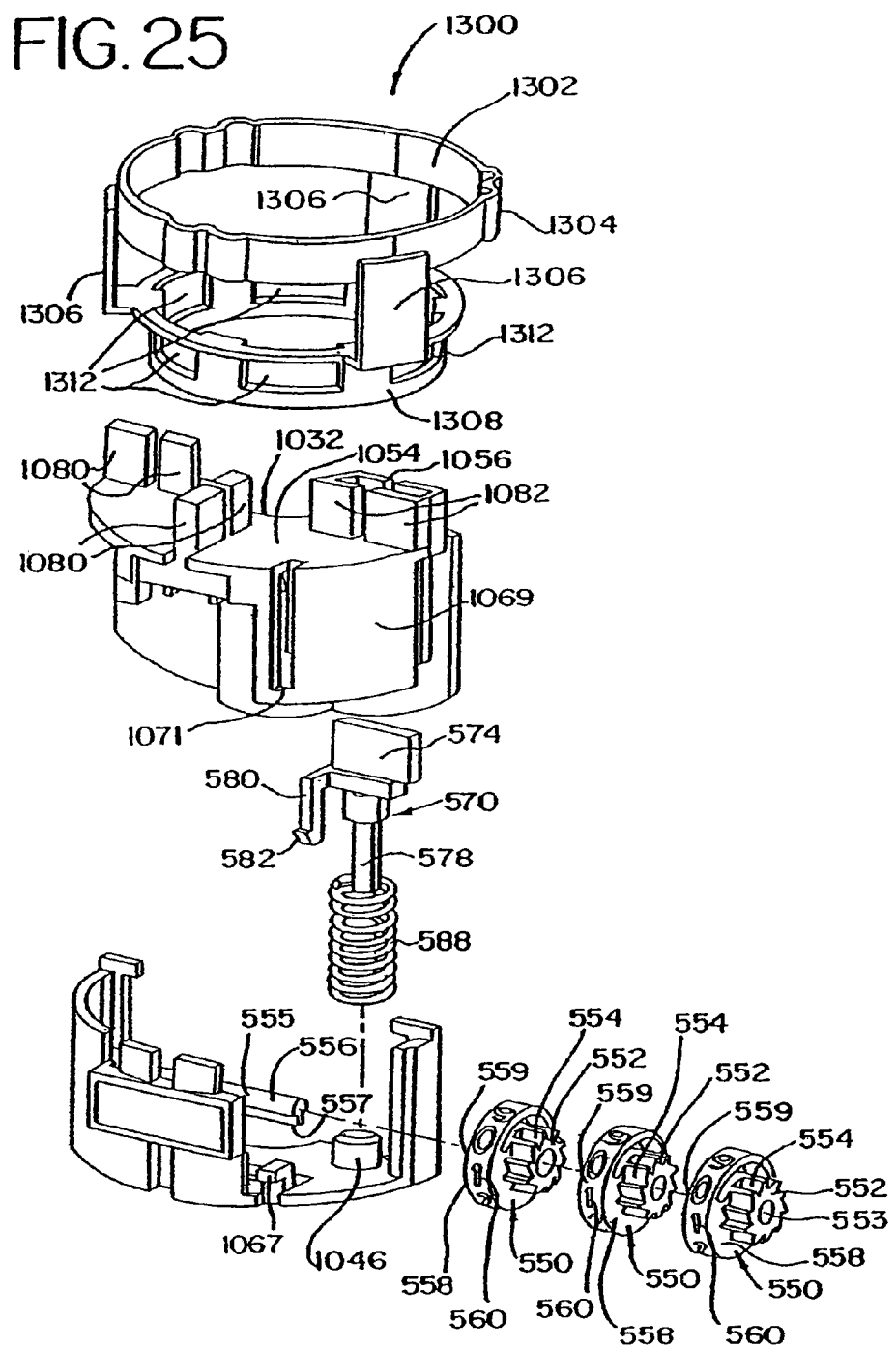

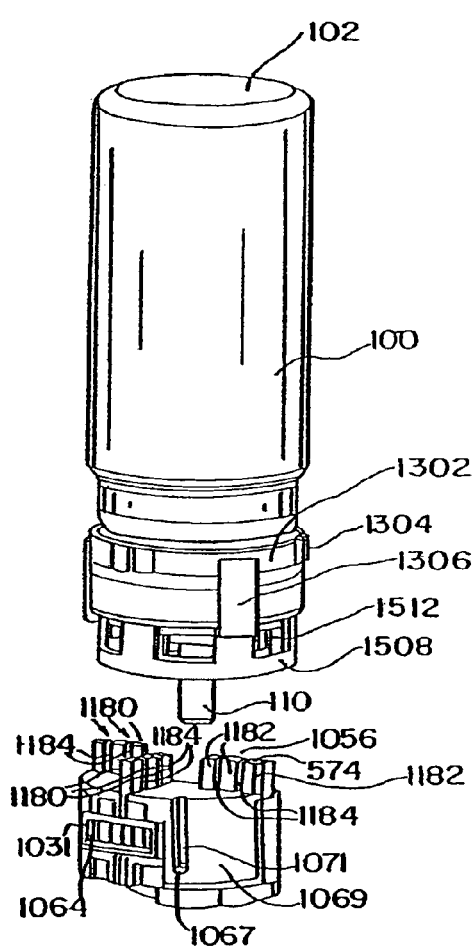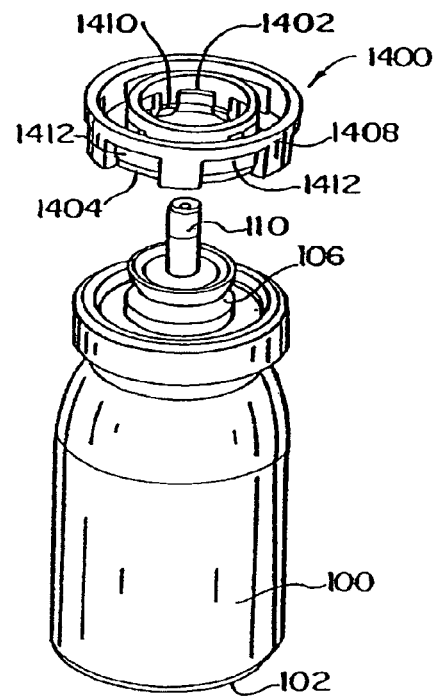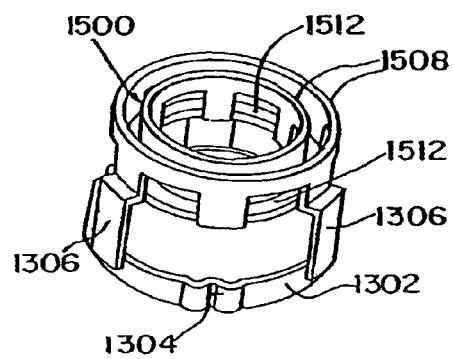

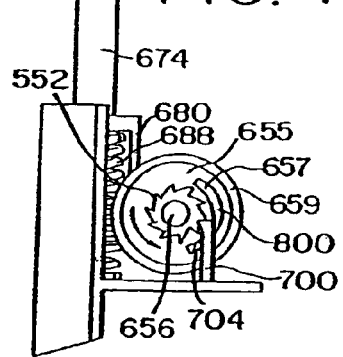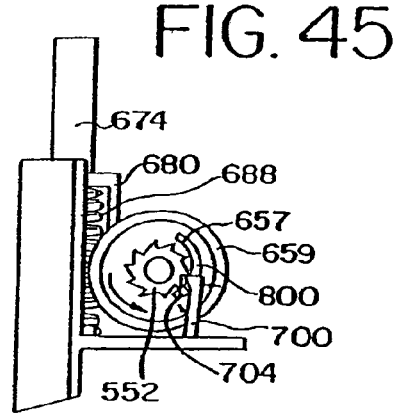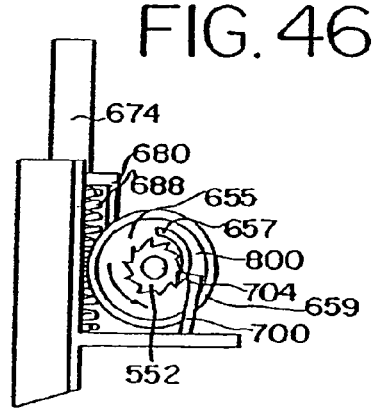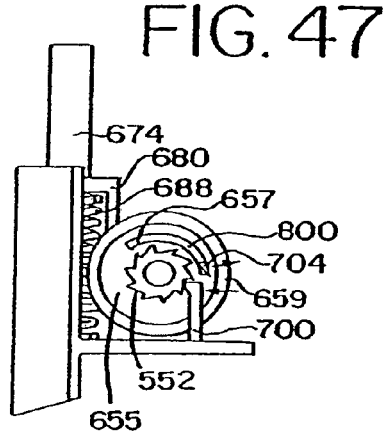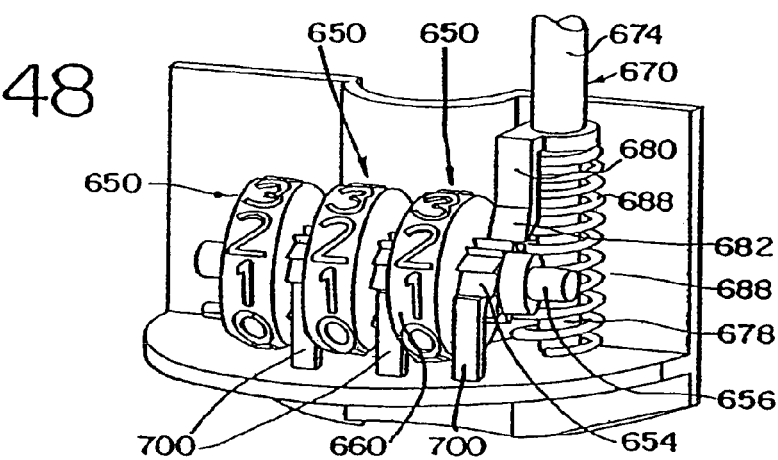

INDICATING DEVICE

This application is a continuation of U.S. application Ser. No. 13/938,009, filed Jul. 9, 2013, which is a continuation of U.S. application Ser. No. 13/431,237, filed Mar. 27, 2012, now U.S. Pat. No. 8,505,773, which is a continuation of U.S. application Ser. No. 13/167,441, filed Jun. 23, 2011, now U.S. Pat. No. 8,157,128, which is a continuation of U.S. application Ser. No. 12/454,564, filed May 19, 2009, now U.S. Pat. No. 7,984,826, which is a continuation of U.S. application Ser. No. 11/287,818, filed Nov. 28, 2005, now U.S. Pat. No. 7,575,130, which is a continuation of U.S. application Ser. No. 10/865,531, filed Jun. 10, 2004, now U.S. Pat. No. 6,997,349, which is a continuation of U.S. application Ser. No. 10/369,091, filed Feb. 18, 2003, now U.S. Pat. No. 6,938,796, which is a continuation of U.S. application Ser. No. 10/193,508, filed Jul. 11, 2002, now U.S. Pat. No. 6,561,384, which is a continuation of U.S. application Ser. No. 09/954,428, filed Sep. 14, 2001, now U.S. Pat. No. 6,435,372, which is a continuation of U.S. application Ser. No. 09/704,959, filed Nov. 2, 2000, now abandoned, which is a division of U.S. application Ser. No. 09/149,708, filed Sep. 8, 1998, now U.S. Pat. No. 6,161,724, which application is a continuation-in-part of U.S. application Ser. No. 09/008,184, filed Jan. 16, 1998, now U.S. Pat. No. 6,142,339, the entire disclosures of which are hereby incorporated herein by reference. No license, expressed or implied, is intended to be granted to application Ser. No. 09/008,184, 09/149,708, 09/704,959, 09/954,428, 10/193, 508, 10/369,091, 10/865,531, 11/287,818, 12/454,564, 13/167,441, 13/431,237 or 13/938,009, or any patents issuing therefrom, by reason of the incorporation of reference herein.

BACKGROUND

The present invention relates generally to an indicating device, and in particular, to an indicating device for indicating the number of metered dosages of a substance, and in particular a medicament, that have been dispensed by, or remain in, a dispensing device.

Delivery systems, and in particular, dispensing devices, have been developed that include a counting or dose indicating device to indicate the number of metered doses of substance that have been dispensed from the delivery system, or to indicate the number of doses remaining therein. For example, patients have certain conditions that can be treated with medicaments dispersed in an aerosol and administered to the patient by inhalation. In one format, the aerosol and medicaments are contained in a container, and dispensed in metered, or measured, dosages with the dispensing device, which can include an actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the dispensing device to, provide an accurate indication of either the number of doses remaining ii the container, or the number of doses already dispensed therefrom.

Typically, a conventional aerosol container includes a body and a valve stem which can be depressed relative to the body so as to emit the metered dose of aerosol and medicament. The container is usually supplied with a predetermined number of metered doses, e.g., on the order of about 200, such that the counting of the number of valve stem depressions, and corresponding number of dispensed metered doses, can be directly correlated with the number of doses remaining in the container.

In operation, the container is typically received within a housing of the dispensing device, wherein the valve is brought into engagement with a support block in the housing. The user administers the medicament by moving the container relative to the housing so as to depress the valve stem and internal valve and thereby release a metered dose, which is typically administered to the user through a port or mouthpiece extending from the housing. In an alternative delivery system, the metered dose can be first discharged into a chamber, and thereafter administered to the patient. After the metered dose is discharged from the container, the valve stem, which is typically spring loaded, biases the container away from the support block so as to again move the container relative to the housing. In this way, a metered dose of medicament is discharged by each cycle of linear reciprocal movement of the container relative to the housing.

Some dispensing devices have indicating devices that convert the linear reciprocal movement of the container relative to the housing into a one-way, or single-cycle, movement of an indicator, wherein the indicator identifies the relative fullness of the container the number of metered doses remaining therein or the number of doses already administered. Although these dispensing devices with indicators have provided the advantage of generally being able to keep track of the number of dosages, there remains room for improvement. For example, indicating devices of this nature may include complex moving parts which can be difficult to assemble and expensive to manufacture. Such devices may also be susceptible to counting inaccuracies due to the configuration of the indexing or mating parts, or require excessive amounts of space within the housing to accommodate the relatively large or numerous moving parts. Others still may impede or interfere with the airflow and medicament being dispensed from the inhalation device. Alternatively, some devices use electrical circuitry to count or record the dispersements. Such devices can be relatively expensive to manufacture, however, and typically require a power source which may be susceptible to damage in various environments, such as moist conditions.

SUMMARY

Briefly stated, in one aspect the invention is directed to a dispensing device having an indicating device. The dispensing device dispenses metered dosages of a substance from a container having a valve moveable between a closed position and an open position. The container dispenses a metered dosage when the valve, actuated by a valve stem, is moved to the open position. In an exemplary embodiment, the dispensing device includes a housing adapted to support the container reciprocally moveable within the housing along a longitudinal axis. The housing has a well adapted to receive the valve stem and an exhaust port. The well communicates with the port such that the metered dosage of substance is dispensed through the port when the valve stem is moved to the open position.

In one embodiment of the indicating device, an indicator assembly includes a worm rotatably mounted in the housing about an axis transverse to the longitudinal axis and responsive to the movement of the reciprocal movement of the container within the housing such that the longitudinal movement of the container relative to the housing causes the worm to rotate about its axis. An indicator member includes dosage indicia visible to a user and a circular gear mounted in the housing about an axis transverse to the axis of the worm and non-parallel to the longitudinal axis. The circular gear engaged the worm.

In a preferred embodiment, the indicator assembly further includes a ratchet wheel rotatably mounted in the housing and adapted to be responsive to the reciprocal movement of the container relative to the housing along the longitudinal axis. The ratchet wheel is connected to the worm such that rotation of the ratchet causes the worm gear to rotate about its axis. In addition, an actuator member including an arm is preferably mounted within the housing and is adapted to move in response to the movement of the container and operably engage the ratchet wheel so as to rotate the wheel in response to the longitudinal movement of the container relative to the housing. Also in the preferred first embodiment, the indicator member includes an indicator wheel coaxially mounted with the circular gear on an axle defining the axis of rotation of the indicator member. The dosage indicia are applied to a surface of the indicator wheel.

In another embodiment of the indicating device, the housing comprises at least one engagement member and the indicator assembly includes a plurality of indicator members, including at least a first and second indicator member. The plurality of indicator members are coaxially mounted in the housing. At least one of the first and second indicator members includes an advancement member, while at least the other of the first and second indicator members includes a plurality of teeth. In operation, the first indicator member is rotated relative to the second indicator member such that the engagement member selectively engages and biases the advancement member into operable engagement with at least one of the plurality of teeth so as to rotate the second indicator member an incremental amount.

In a preferred embodiment, an actuator member is mounted in the housing and is responsive to the movement of the container. The actuator member selectively engages at least one of the plurality of teeth on the first indicator member so as to advance the first indicator member an incremental amount in response to the movement of the container relative to said housing. A spring is preferably disposed in the housing to bias the actuator member into engagement with the container.

In another aspect of the invention, the indicator assembly, including the ratchet wheel, worm, actuator member and indicator member of the first embodiment, are mounted within an indicator module which is adapted to be mounted within the dispenser housing. Similarly, with respect to the second embodiment, the indicator assembly, including the plurality of indicator members, advancement member, spring and ratchet member, are supported in the Indicator module. The module preferably includes a first and second member which are joined to form an enclosure or housing, and which support any one or more of the ratchet wheel, worm, actuator member and indicator member of the first embodiment therein, or the plurality of indicator members, advancement member, spring and actuator member of the second embodiment. In the second embodiment the engagement members are also preferably disposed in the module housing.

In another aspect of the invention, a key member is mounted to one of the container and the housing and is shaped to be received in a passageway formed in the other of the housing and container.

In yet another aspect of the invention, a method is provided for dispensing measured dosages from the container. In one embodiment, the method includes the steps of moving the container along the longitudinal axis so as to move the valve stem, and valve, to the open position wherein a metered dosage is discharged. The longitudinal movement of the container within the housing causes the ratchet gear to rotate a predetermined angular amount, which, in turn, causes the worm to rotate about its axis. The worm then engages the circular worm gear of the indicator member so as to rotate the worm gear about its axis.

Alternatively, in a second embodiment, the first indicator member is rotated a predetermined amount in response to the movement of the valve between a closed and open position, or vice versa. Upon a predetermined number of movements of the valve, the first indicator member causes the second indicator member to rotate a predetermined amount.

In another aspect of the invention, a method is provided for assembling a dispenser comprising a housing, a container and an indicator module.

In yet another aspect of the invention, a kit includes components capable of being assembled as a dispensing device for dispensing metered dosages of a substance from a container. The kit includes a housing, a container having a plurality of metered dosages of the substance and an indicator module having an indicator member.

The present invention provides significant advantages over other indicating devices. In particular, with respect to the first embodiment of the indicating device, the worm provides for a compact drive component that does not occupy excess space within the housing. Moreover, the worm provides for high gear reduction ratios while maintaining a continuous engagement with the circular worm gear. The continuous engagement of the worm and circular gear ensures that the accuracy of the counting device is maintained, while simultaneously simplifying the manufacturing and assembly process:

The use of a circular gear having an axis non-parallel, and preferably transverse or perpendicular to the longitudinal movement of the container within the housing, also provides several advantages. Importantly, the gear can be easily mounted to the housing with an inexpensive and easy-to-install axle. Thus, the circular gear provides for a compact single-cycle device that fits easily into the housing, and which maintains continuous engagement with the worm gear for improved and accurate indexing of the indicator member. Moreover, the components are arranged so as to not interfere with or otherwise impede the air flow from the valve stem to the exhaust port of the housing. In addition, the indicator wheel, which is preferably coaxially mounted with the worm gear, provides an ideal planar surface for displaying the dosage indicia. The indicia can be easily viewed by the user through the viewing window.

The second embodiment of the indicating device provides similar advantages. In particular, the plurality of indicator members can be mounted in a compact arrangement to provide accuracy and reliability under various operating conditions but which does not impede or obstruct the airflow to the user. Moreover, the various parts are relatively inexpensive to manufacture and assemble. The indicia, which are visible to the user through the viewing window, are easy to read and readily accessible to the user.

The indicator module, with any of the various embodiments of indicating assemblies disposed therein, also presents several advantages. In particular, the self-contained unit can be separately manufactured and installed as needed in any number of conventional types of dispensing devices with minimal modification thereof. Moreover, the module can be easily installed without interfering with or otherwise impeding the air flow from the valve stem to the exhaust port and ultimately to the user.

The key member also presents several advantages. In particular, differently configured key members and passageways can be installed between containers holding different substances such as medicaments and corresponding delivery system housings so as to prevent the user from interchanging various containers and housings so as to thereby alter the number of doses being counted. The key member and passageway can also prevent a user from using the wrong delivery system for a particular container having a particular substance, such as a medicament.

The present invention, together with further objects and advantages, will be best understood by reference to the following detailed description taken in conjunction with the accompanying drawings.

BRIEF DESCRIPTION OF THE DRAWINGS

FIG. 1 is a perspective view of a dispensing device with a viewing window revealing dosage indicia.

FIG. 2 is a perspective view of one embodiment of the dispensing device with a portion of the housing cut away.

FIG. 3 is a perspective view of one embodiment of the indicator assembly.

FIG. 6 is a perspective view of a container, a dispenser housing and one embodiment of an indicator module with a portion of the housing cut away.

FIG. 7 is an exploded perspective view of a container, a dispenser housing and one embodiment of the indicator module with a portion of the housing cut away.

FIG. 8 is an exploded perspective view of one embodiment of the indicator module.

FIG. 9 is an exploded perspective view of the indicator module, from the opposite side as shown in FIG. 8.

FIG. 13 is a top view of one embodiment of the indicator module.

FIG. 14 is a rear view of the indicator module shown in FIG. 13.

FIG. 15 is a cross-sectional view of the indicator module taken along line 15-15 of FIG. 13.

FIG. 16 is a cross-sectional view of the indicator module taken along line 16-16 of FIG. 13.

FIG. 17 is a cross-sectional view of the indicator module taken along line 17-17 of FIG. 13.

FIG. 18 is a crossectional view of the indicator module taken along line 18-18 of FIG. 13.

FIG. 19 is a perspective view of an alternative embodiment of the module.

FIG. 20 is a cross-sectional view of the indicator module taken along line 20-20 of FIG. 14.

FIG. 21 is an exploded view of a container, a key member and an indicator module.

FIG. 22 is a top view of the key member.

FIG. 23 is a cross-sectional view of the key member taken along line 23-23 of FIG. 22.

FIG. 24 is a perspective view of a container and an alternative embodiment of the indicator module mounted in a dispenser housing with a portion of the housing cut away.

FIG. 25 is an exploded perspective view of an alternative embodiment of an indicator module, key member and indicator assembly.

FIG. 32 is a perspective view of a container with an alternative embodiment of a key member installed thereon positioned above one embodiment of an indicator module.

FIG. 33 is a perspective view of an alternative embodiment of the key member.

FIG. 34 is an exploded perspective view of an alternative embodiment of a key member being applied to a container.

FIG. 44 is a cross-sectional view of an advancement member on a first indicator member, a second indicator member and an engagement member.

FIG. 45 is a cross-sectional view of the advancement member as it is first engaged by the engagement member.

FIG. 46 is a cross-sectional view of the advancement member as it is biased by the engagement member into engagement with the indicator member.

FIG. 47 is a cross-sectional view of the advancement member as it is further biased by the engagement member into engagement with the second indicator member.

FIG. 48 is a perspective view of an alternative embodiment of an indicator assembly disposed on a lower member of the module housing.

DETAILED DESCRIPTION OF THE PRESENTLY PREFERRED EMBODIMENTS

Figure 4:
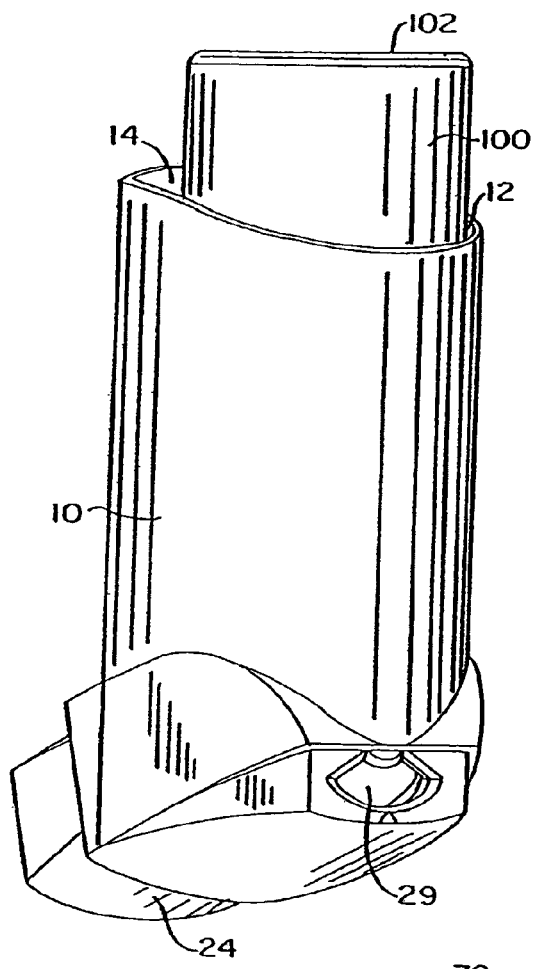
FIG. 4 is a perspective view of an alternative embodiment of the dispensing device.

Referring to the drawings, and in particular FIGS. 1, 4, 6, 7 and 24, a delivery system, configured as a dispensing device, or dispenser, is shown as including a housing 10, or actuator boot, and a container 100 disposed therein. The housing 10 has a longitudinally extending cavity 12 shaped to receive the container. A top portion of the housing is generally open such that the container can be inserted in the housing through opening 14 and be installed therein with a bottom end 102 of the container protruding from the housing and exposed to the user for actuation.

It should be understood that the term "delivery system," as used herein, is meant to include a system or apparatus for delivering a substance from a container, reservoir, or similar repository, to a user, and includes but is not limited to the disclosed dispensing device, which delivers the substance to the user in the form of an aerosol that is inhaled by the user. The term "dispensing device," as used herein, is meant to include devices that extrude, spray or otherwise feed out or deliver a substance in convenient units, and includes, but is not limited to, the disclosed inhalation device which delivers metered dosages of a substance in aerosol form for inhalation by the user.

The term "longitudinal" as used herein is intended to indicate the direction of the reciprocal movement of the container relative to the housing. The terms "top", "bottom," "upwardly" and "downwardly" are intended to indicate directions when viewing the inhalation devices as shown in the Figures, but with the understanding that the container is inverted such that the top surface thereof is located adjacent the bottom of the housing and vice versa.

Figure 5:
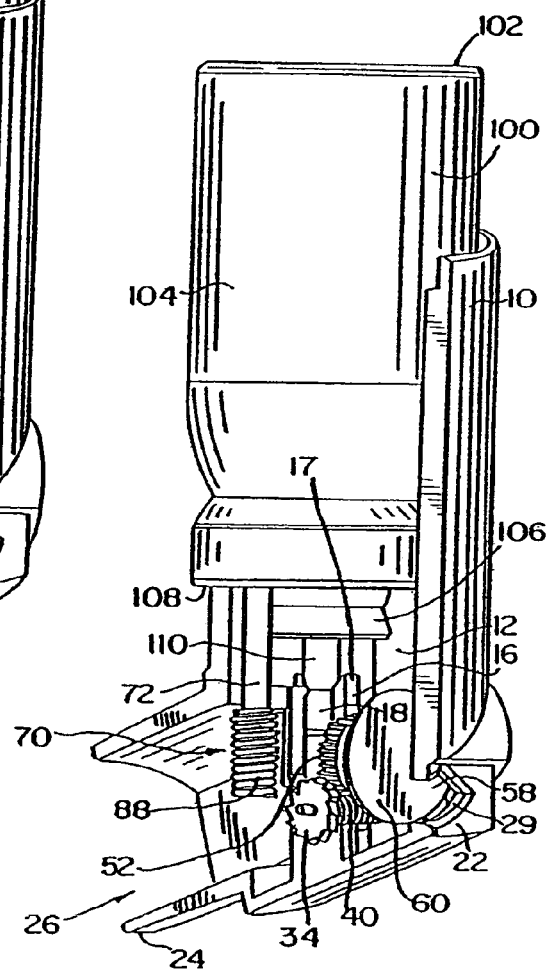
FIG. 5 is a perspective view of the dispensing device shown in FIG. 4 with a portion of the housing cut away.

As shown in FIGS. 5, 6 and 7, a cylindrical support block 16 having a well 18 is formed in a bottom portion 22 of the housing. An orifice 20 penetrates the support block to communicate with a bottom portion of the well. A mouthpiece 24, intended for insertion into the mouth of a patient, forms an exhaust port 26 that communicates with the orifice and well. The mouthpiece 24 extends laterally from the housing so as to facilitate insertion of the mouthpiece into the mouth of the patient.

The container 100 is formed as a cylindrical canister 104 having a 106 hub disposed on a top surface 108 thereof. A valve stem 110 extends longitudinally from the hub. The valve stem extends coaxially from the canister and is biased outwardly therefrom by a spring (not shown) mounted within the canister. The container 100 is mounted in the housing by press fitting the valve stem 110 in the well 18 of the support block. It should be understood that the container can be configured in a variety of shapes and sizes, and that the substance contained therein can be released by any number of valve systems that are well known in the art. It should also be understood that the valve system can be actuated by a variety of actuators, including, but not limited to, various pumps, levers, actuator boots, buttons and the like. In such embodiments, the valve system can be actuated by an actuator moveable relative to the container and housing such that the container remains stationery relative to the housing.

In a preferred embodiment, the container 100 is filled with a substance which is dispensed therefrom in specific metered doses by depressing or moving the valve stem 110 from an extended closed position to a depressed open position, which in turn opens the valve or valve system. Preferably the substance is a medicament, although it should be understood that the container could be used to hold a variety of non-medicinal substances, including but not limited to, various liquids, foams or aerosols that can be delivered by various delivery systems, and/or dispensing devices. A medicament is defined as a substance that can be used in therapy, such as for various therapeutic treatments, including the treatment of diseases (e.g., respiratory ailments) and for the relief of pain, and should be understood to include medicines and medicinal substances in general. A single metered dose is dispensed from the container by each reciprocal, longitudinal movement of the valve stem and attendant opening and dosing of the valve. The medicament is typically delivered to the user, or patient, through their mouth and/or nose in the form of an aerosol, spray or liquid.

In operation, the opening of the valve stem and valve is effected by moving the container 100 reciprocally within the housing 10 along a longitudinal axis, defined by the valve stem and the reciprocal movement of the container, by depressing the exposed bottom end 102 of the canister relative to the housing 10 so as to move the valve stem 110 to the open position as it is supported within the well by the support block. Alternatively, an actuator can be moved to open the valve system of the container, which can remain stationary with respect to a supporting housing, a cap and/or an indicating device mounted thereto. For example, the actuator can be attached to the end of the container in the form of a pump device or the like.

Referring to FIGS. 5-7, as the valve stem is moved to the open position, the container dispenses a metered dose of the substance in aerosol form through the well 18 and orifice 20 and into the exhaust port. The substance in aerosol form is then transmitted to the user through the exhaust port of the mouthpiece by way of either a self-generated or assisted airflow. Alternatively, metered doses of liquids and the like can be dispensed from the container.

In other delivery systems, which may also include a dispensing device, the housing and holder for the container are attached to a component having a chamber with an output end. Examples of these kinds of delivery systems and dispensing devices are shown for example in U.S. Pat. No. 5,012,803, issued May 7, 1991, and U.S. Pat. No. 4,460,412, issued Sep. 11, 1984, the entire disclosures of which are hereby incorporated herein by reference. (No license, expressed or implied, is intended to be granted to either of these patents by reason of the incorporation by reference herein.) In these kinds of delivery systems, the component having the chamber can be adapted to receive the mouthpiece of the housing, or it can be integrally connected with a holder supporting the container. In either embodiment, the metered dose of substance, preferably a medicament, in aerosol is first dispensed torn the container into the chamber, and thereafter inhaled by the user.

In a preferred embodiment, the container 100 is intended to dispense a predetermined number of metered doses of substance. For example, conventional inhaler containers typically hold on the order of 100 to 200 metered doses. In operation, it is important that the user be aware of the number of metered doses remaining in the container such that the user is not caught unaware with an empty canister when in need of the substance, such as a medicament.

Now referring to FIGS. 2 and 3, a dispensing device, configured as an aerosol dispenser, is shown as including a housing, a container mounted therein as described above and an indicator assembly. The indicator assembly includes a ratchet gear 32 coaxially mounted with a worm 40 on an axle 42 in a lower portion of the housing. A plurality of teeth 34 are formed about the periphery of the ratchet gear. The teeth 34 are cut or formed with a tapered surface 36 and engagement surface 38. In a preferred embodiment, the ratchet and worm are formed out of a hard durable plastic. It should be understood, however, that other materials such as metal would also work. The ratchet and worm can be made as separate parts, or molded as a single integral member.

In a preferred embodiment, the axle 42 and worm 40 define an axis of rotation transverse, or perpendicular, to the longitudinal axis defined by the valve stem and reciprocal movement of the container relative to the housing. Opposite ends of the axle 42 are rotatably supported in the housing.

Also as shown in FIGS. 2 and 3, an indicator member 50 comprises a circular worm gear 52 and indicator wheel 58 coaxially mounted on an axle. In a preferred embodiment, the axle 56 defines an axis of rotation transverse to the axis defined by the worm and also transverse to the longitudinal axis defined by the reciprocal movement of the container relative to the housing. The axle 56 is rotatably supported in the housing. Teeth 54 are formed around the periphery of the worm gear 52 and are shaped to permanently engage the worm 40. As shown in FIG. 2, the indicator wheel 58 has a planar face 60 which is exposed to the patient through a viewing window 28 formed in the housing.

Figure 12:
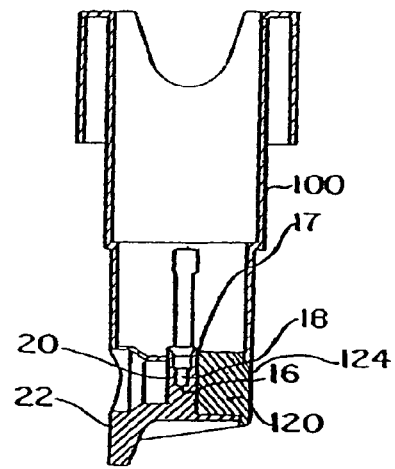
FIG. 12 is a section cut of a housing and an indicator module mounted therein.
Figure 26:
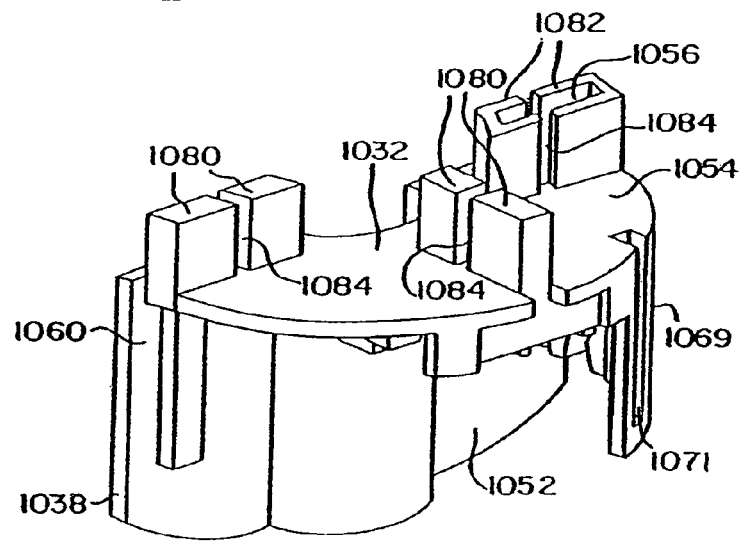
FIG. 26 is a top perspective view of a first member of one embodiment of the indicator module housing.

The ratchet gear 32, worm 40, worm gear 52 and indicator wheel 56 provide an ideal arrangement for indicating the number of doses remaining in the container, or the number dispensed therefrom. In particular, relatively high reduction ratios are made possible through use of the ratchet, worm and worm gear without the corresponding requirement of providing extremely fine teeth on one or more of the ratchet gear and worm gear. Moreover, the worm and worm gear interface avoids the associated inaccuracies introduced by the mating, and potential skipping, of conventional spur gears having fine teeth. Furthermore, the installation of the indicator member is effected by the installation of a simple axle which can be supported in a plurality of positions and angular orientations within the housing. Importantly, the high reduction ratio realized with the worm 40 allows for the worm gear 52 to have a relatively small diameter, such that it can be easily mounted within small spaces within the housing. Indeed, as shown in FIGS. 6 and 12, the entire indicator assembly can be mounted behind the support block 16 and below the upper surface 17 thereof such that the assembly does not interfere with the dispensing of the medicament from the orifice or with the airflow generated by the patient in administering the medicament.

Referring to FIG. 5, an actuator member 70 is configured as a post member 72 moveably supported in the housing along an axis parallel to the longitudinal axis defined by the reciprocal movement of the container within the housing. In an alternative embodiment shown in FIGS. 7-9, the post member includes an upper portion 74, a middle portion 76 and a lower portion 78. A resilient arm member 80 extends from the middle portion of the post member and terminates in a tapered hook member 82 shaped to selectively engage one of the ratchet wheel teeth. The middle portion 76 is defined by upper and lower slop surface 84, 86. A spring 88 is disposed about the lower portion 78 of the post member and engages the lower stop surface 86 so as to bias the actuator member upwardly against the top surface 108 of the canister as shown in FIG. 7. Although a compression spring is shown in the Figures, it should be understood that cantilever, torsion, leaf and tension springs, and the like, would also work to bias the actuator member upwardly into engagement with the container. The springs can be made of metal or plastic.

In an alternative embodiment, shown in FIGS. 2 and 3, actuator member 90 includes locking ring 92 and a resilient arm member 94 extending longitudinally downwardly therefrom. A longitudinal slit 96 is formed in the locking ring so as to allow for the locking ring 92 to be expanded and disposed around the hub 106 (shown in FIG. 5) of the canister in a snap fit configuration such that the valve stem of the container extends through opening 98 of the locking ring. A distal end of the resilient arm member terminates in a hook member 95 which is shaped to selectively engage the teeth of the ratchet wheel.

In the operation of the embodiment shown in FIGS. 6-9, 13-18 and 20, the container is moved longitudinally within the housing so as to depress the valve stem to the open position so as to open the valve as explained above. As the container is moved downwardly within the housing, the actuator member 70 is moved longitudinally downward such that the hook member 82 engages the ratchet wheel and rotates it a predetermined angular amount corresponding to the pitch of the teeth. When the container is released by the user, the spring (not shown) within the container biases the container upwardly within the housing along the longitudinal axis such that the valve stem 110 is moved to the closed position within the container so as to close the valve. As the container moves upwardly, the resilient arm member 80 is biased laterally outward as a tapered end portion of the hook member 82 slides against the tapered surface 36 of one of the ratchet teeth. As the container and resilient arm member reach the top of the stroke, wherein the valve stem is moved completely to the closed position, the resilient arm member 80 returns to its normal straightened configuration as the hook member 82 slips past the tapered surface of one of the teeth so as to be positioned over the engagement surface 38 of that tooth 34 for the next cycle.

Alternatively, the operation of the ratchet wheel can be reversed as shown in FIG. 3. In this embodiment the resilient arm member 94 is biased-outwardly by the tapered surface of one of the ratchet gear teeth on the downstroke. At the bottom of the stroke, the hook member 95 sips into an underlying relationship with the engagement surface of the tooth. When the container is released by the user, the spring (not shown) within the canister biases the container upwardly within the housing along the longitudinal axis such that the valve stem is moved to the closed position within the container. As the container moves upwardly with respect to the housing, the resilient arm member 94 moves longitudinally upward such that the hook member 95 engages the engagement surface 38 of one of the teeth and thereby rotates the ratchet wheel an incremental amount.

In the embodiment shown in FIGS. 6-9, 13-18 and 20, it is the force of the spring 88 that moves the arm member 80 upwardly so as to return the actuator member in preparation for another cycle. In the alternative embodiment shown in FIGS. 2 and 3, it is the movement of the container, as it is biased upwardly by the internal spring acting on the valve stem, that causes the locking ring 92 and arm member 94 to move upwardly and thereby rotate the ratchet gear.

Referring to FIGS. 8 and 17, a resilient non-return member 200 engages the ratchet gear adjacent the hook member so as to ensure that the rotation at the ratchet gear is unidirectional. Alternatively, the non-return member can be positioned to engage the ratchet gear opposite the actuator arm member. The non-return member includes an end portion adapted to engage the engagement surface of the ratchet gear teeth. As the ratchet gear is rotated by the actuator, the non-return member slides along the tapered surface of one of the teeth of the ratchet wheel and does not interfere with the rotation thereof.

The rotation of the ratchet gear causes the worm 40 to rotate a desired predetermined amount. It should be understood that the desired amount of rotation is dependent upon the diameter of the ratchet wheel and the number of teeth positioned thereabout. Rotation of the worm, which permanently engages the teeth of the worm gear, causes the worm gear and indicator wheel to rotate a predetermined incremental amount. The amount of rotation of the indicator wheel is dependent upon the pitch of the worm, the number of worm threads and the pitch of the worm gear and the number of warm gear teeth. In a preferred embodiment, the worm has a single thread.

For ease of manufacturing, it is desirable to provide as coarse a pitch on each of the ratchet and worm gears as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the canister, it is important for the ratchet, worm and worm gear to provide a relatively high reduction ratio, such that 200 linear reciprocal movements of the actuator member correspond to one or less revolutions of the indicator member. Because the ratchet gear and worm rotate together, it should be understood that the number of teeth on the ratchet gear and worm gear, and the number of threads of the worm, determine the ultimate reduction ratio between the rotation of the ratchet gear and the rotation of the indicator wheel.

For example, when the container holds 240 metered doses, an acceptable ratio is realized if the ratchet is made relatively coarse with 10 teeth and the worm gear is provided with 28 teeth. In operation, the dispensing of 10 metered doses will cause the worm to make one complete revolution so as to thereby move the worm gear one tooth. After 240 linear reciprocal movements, the worm gear has been advanced by 24 teeth. Extra teeth are provided so that the starting and ending indicia, indicating a relative fullness or emptiness of the container respectively, are not labeled one on top of the other.

In a preferred embodiment, shown in FIGS. 9 and 15, the worm gear 52 has teeth formed around only a portion of its periphery so that a gap is formed between the teeth around the remaining portion of the periphery. In operation, the gears are configured so that the worm 40 disengages from the last tooth of the worm gear as the final prescribed dose of medicament is dispensed. In this position, the indicia on the indicator wheel 58 will indicate to the user that the canister is empty. Therefore, although the user can continue to move the container so as to open the valve, the resultant movement of the actuator 70, ratchet gear 32 and worm will not in turn rotate the indicator member as the gap in the teeth on the worm gear results in the disengagement of the worm and worm gear. In this way, the indicator wheel is prevented from being inadvertently rotated from a full to empty reading and then back again to a full reading, which could confuse the user about the number of doses remaining in the canister.

Figure 10:
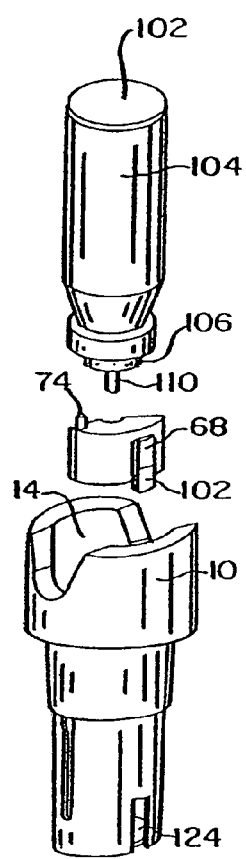
FIG. 10 is an exploded perspective view of a container, and an alternative embodiment of the dispenser housing and the indicator module.

The indicator wheel 58, indicia 66 and viewing window 28 can be arranged in a variety of configurations for viewing by the user. For example, the viewing window 28, 124 can be configured as a rectangular shaped window as shown in FIG. 2 or 10 respectively, as an arcuate shaped window 29 as shown in FIG. 4, wherein approximately ⅓ of the face of the indicator wheel is visible at any time, as a circular shaped window (not shown) or as any other shape allowing the user to view the indicator wheel and the indicia located thereon.

In one embodiment, the indicia take the form of a color code, where, for example, a portion of the wheel is colored green to indicate the starting full position, a portion is colored yellow to indicate a medium fullness and a portion is colored red to indicate that the container is empty. Obviously, other colors, shading or alpha-numerical indicia can be provided on the indicator wheel to indicate the relative-fullness or emptiness of the container.

In an alternative embodiment, the indicator wheel can be oriented within the housing such that either its planar face or its circumferential surface, with indicia applied thereto, are visible to the user through the exhaust port of the mouthpiece.

Figure 28:
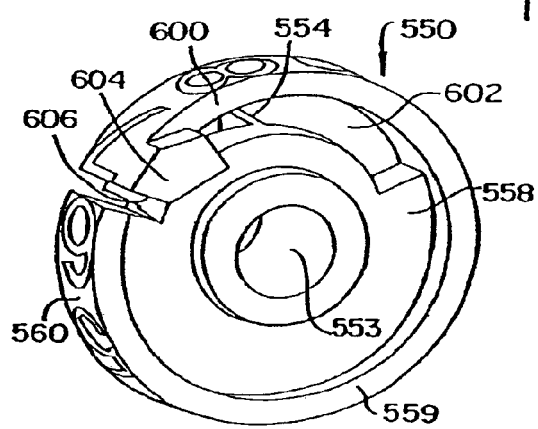
FIG. 28 is a perspective view of one embodiment of an indicator member.
Figure 29:
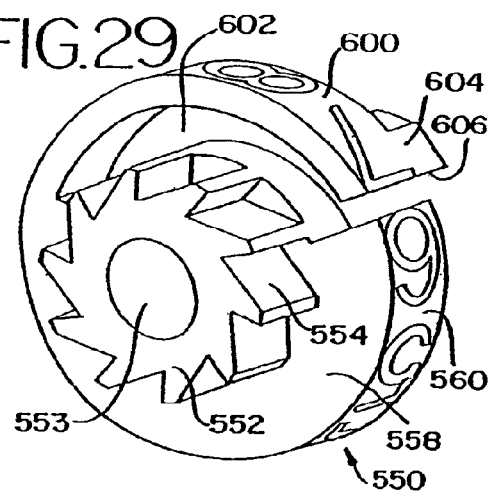
FIG. 29 is an opposite perspective view of the indicator member shown in FIG. 28.

Referring to FIG. 25, an alternative embodiment of an indicator assembly is shown. The indicator assembly includes three indicator members 550 coaxially mounted on an axle 556 and rotatable thereabout. As best shown in FIGS. 28 and 29, each of the indicator members includes an indicator wheel 558 having a circumferential skirt 559 with an outer circumferential surface 560 on which indicia (shown as numbers) are applied, and a ratchet gear 552 coaxially mounted with the indicator wheel. The indicator wheel and ratchet gear have an opening 553 shaped to receive the axle. The ratchet gear 552 includes a plurality of teeth 554 formed around its periphery. The ratchet gear is preferably integrally molded with the indicator wheel, although it should be understood that the gear and wheel can be made separately and thereafter attached one to the other by welding, adhesive and the like.

In one embodiment of the indicator member, a resilient advancement member 600 is formed from a portion of the circumferential skirt 559 by providing an elongated cutout 602 in the indicator wheel radially inward from and beneath the skirt. The advancement member 600 includes a laterally extending tooth portion 604 having an engagement surface 606. The three indicator members are coaxially mounted such that the tooth portion 604 of the advancement member of a first indicator member overlies the ratchet gear teeth 554 of the second indicator member, and such that the tooth portion 604 of the advancement member of the second indicator member overlies the ratchet gear teeth 554 of the third indicator member. When only three indicator members are used (as shown in FIG. 25), the third indicator member does not require an advancement member, although for the sake of simplicity in manufacturing, a modular indicator member with the same indicia applied thereto and the same advancement member formed thereon is preferably used for each of the first, second and third indicator members. It should be understood by one of skill in the art that one or more indicator members may be used to provide an indication of dosages used or available, and that the three indicator members shown in the Figures is meant to be illustrative, rather than limiting. In addition, it should be understood that a plurality of indicator members refers to any number of indicator members greater than one.

Figure 39:
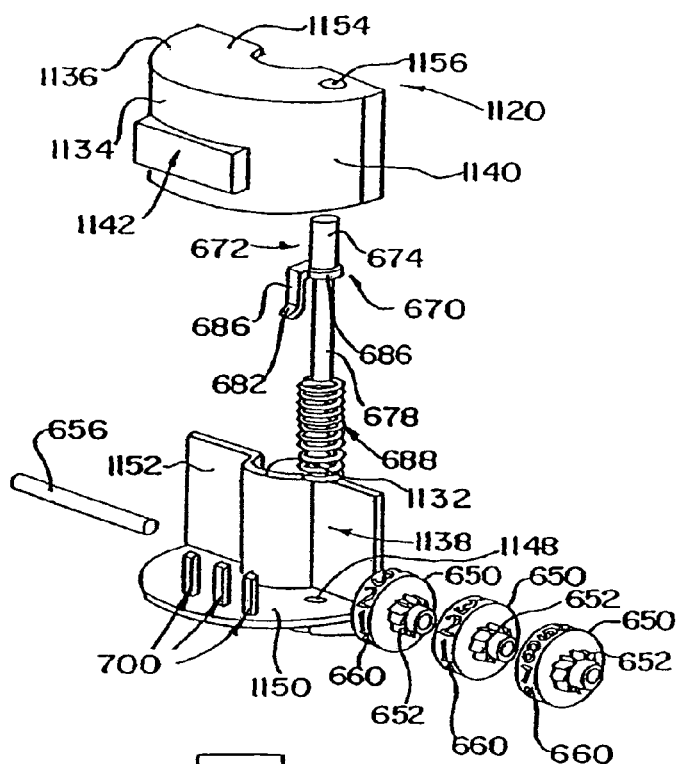
FIG. 39 is an exploded perspective view of an, alternative embodiment of an indicator module and indicator assembly.
Figure 42:
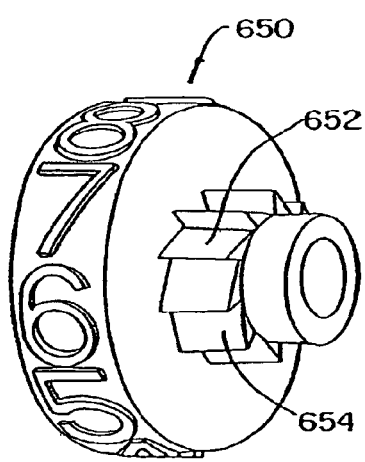
FIG. 42 is a perspective side view of an alternative embodiment of an indicator member.
Figure 43:
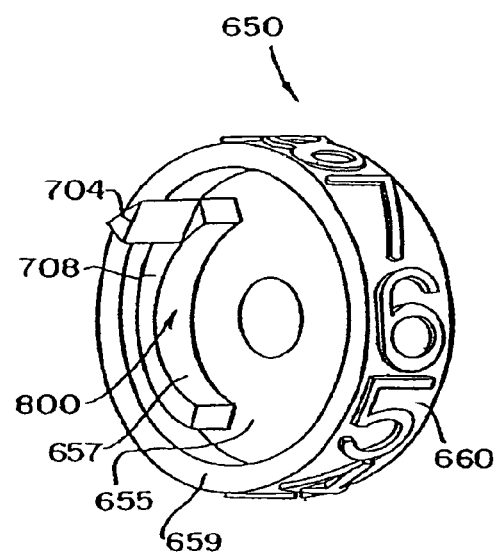
FIG. 43 is an opposite perspective side view of the indicator member of FIG. 42.

In an alternative embodiment of the indicator member 650, shown in FIGS. 39, 42 and 43, an advancement member 800 is disposed radially inward from a circumferential skirt 659 and includes a first end 657 connected to a planar side portion or hub 655 of the indicator wheel. The advancement member includes a curved resilient portion 708 having a free end with a tooth portion 704 extending laterally outward therefrom so as to extend laterally from beneath the skirt 659 of the indicator wheel such that it overlies the teeth of the ratchet gear of an adjacent indicator member coaxially mounted therewith as shown in FIG. 48. Indicia, preferably in the form of numbers, are applied to the circumferential surface 660 of the skirt. A ratchet gear 652, having a plurality of teeth 654 is coaxially mounted with the indicator wheel. As shown in FIG. 48, three indicator members are coaxially mounted on axle 656.

Referring to FIGS. 25 and 39, an actuator member 570, 670, otherwise referred to as a ratchet member, is shown as having an upper portion 674, 674 extending upwardly from a lower portion 578, 678 and a resilient arm member 580, 680 extending outwardly therefrom and terminating in a resilient hook member 582, 682 shaped to selectively engage at least one of the teeth of the ratchet gear of the first indicator member. A spring 588, 688 is disposed around the lower portion of the actuator member and biases the upper portion 574, 674 of the actuator member into engagement with the container.

Figure 27:
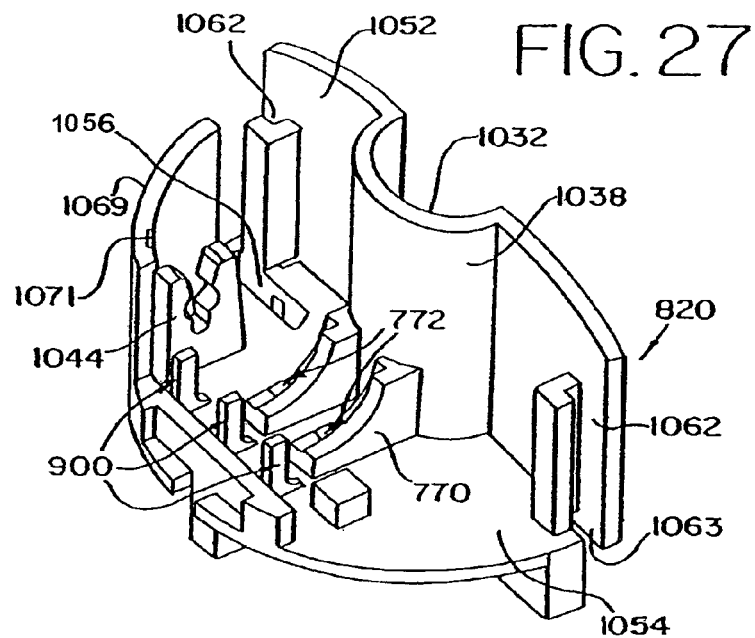
FIG. 27 is a bottom perspective view of the member shown in FIG. 26.

Referring to FIG. 27, a housing 820 is shown as having a pair of engagement members 770 formed integrally with the housing and including ramped surfaces 772. A plurality of non-return members 900 extend from the housing and selectively engage the ratchet gear to ensure unidirectional rotation of the indicator member as shown in FIGS. 35-38. Although the engagement members and non-return members are shown as being formed in or extending from a module housing, as described below, one of skill in the art should understand that those members or equivalent features could also be formed in or connected to the dispenser housing or actuator boot that supports the container, or disposed on or connected to the container itself.

Referring to FIGS. 25 and 35-38, the operation of the indicator assembly shown in FIG. 25 is generally shown. In particular, the container is moved longitudinally within the housing 10 so as to depress the valve stem 110 to the open position so as to open the valve as explained above. As the container is moved downwardly within the housing, or downwardly with respect to the module housing described below, the actuator member 570 is moved longitudinally downward such that the hook member 582 is biased outwardly by the ratchet gear 552 on a first outer indicator member. At the bottom of the stroke, the hook member 582 silos into an underlying relationship with the teeth on the ratchet gear. When the container is released by the user, the spring (not shown) within the container biases the container upwardly within the housing along the longitudinal axis such that the valve stem 110 and valve are moved to the closed position within the container. As the container moves upwardly, the resilient arm member 580 moves longitudinally upward such that the hook member 582 rotates the first indicator member a predetermined angular or incremented amount corresponding to the pitch of the teeth disposed around the periphery of the ratchet gear. As the container and resilient arm member reach the top of the stroke, wherein the valve stem and valve are moved completely to the closed position, the resilient arm member 580 is positioned over the ratchet gear for the next cycle. Alternatively, the operation of the actuator member and ratchet gear can be reversed as explained above with respect to the embodiment shown in FIGS. 6-9.

Figure 40:
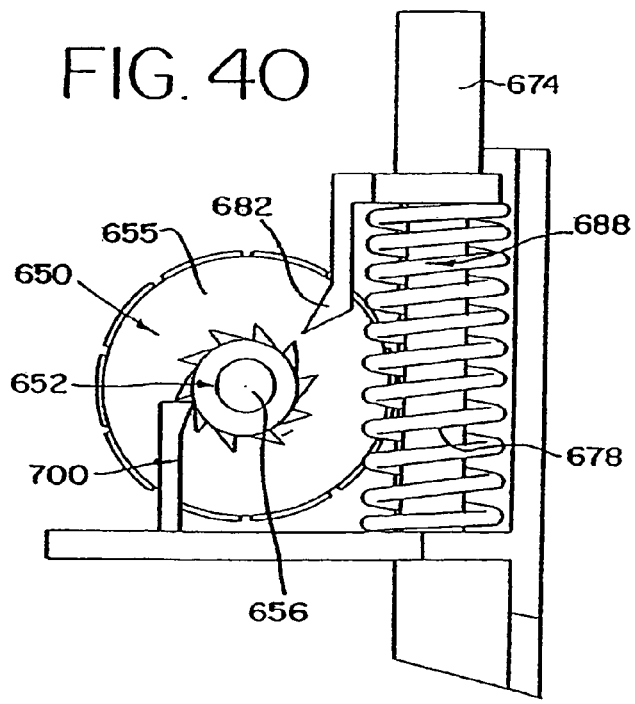
FIG. 40 is an enlarged side view of an actuator member in a disengaged position adjacent a first indicator member.
Figure 41:
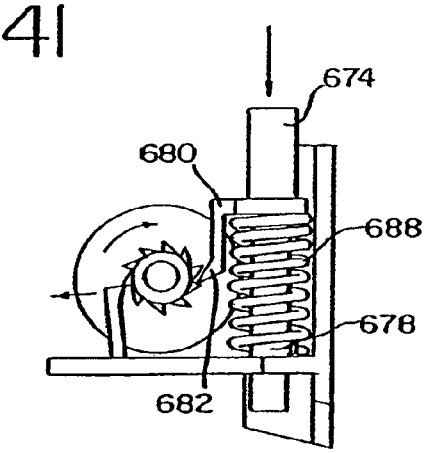
FIG. 41 is a side view of the actuator member engaging the first indicator member with the non-return being biased outwardly.

Referring to FIGS. 39-41 and 44-48, a plurality of resilient arm members 700 are shown as extending from a module housing so as to be aligned with the ratchet gears on each of the indicator members. The arm members 700 each serve as a combined engagement member and non-return member. In particular, as shown in FIGS. 40 and 41, the arm member 700 functions as a non-return member and includes an end portion that is biased away from the teeth on the ratchet gear as the actuator member, or adjacent indicator member with its advancement member, is actuated to advance the ratchet gear. The Operation of the actuator member 670 and ratchet gear is similar to the operation of the ratchet gear shown in FIGS. 6-9 as explained above. The arm member 700 snaps back so that the end portion engages one of the teeth of the ratchet gear so as to ensure that the rotation of the ratchet gear is unidirectional. As shown in FIGS. 44-47, the arm member 700 overlying the ratchet gears of the second and third indicator members also serves as an engagement member that selectively engages the advancement members connected to the indicator members.

In operation, the reciprocal movement of the container relative to the housing is repeated until the first indicator member 550, 650, an its ratchet gear, are rotated one complete revolution. The predetermined number of reciprocal movements required to advance the first indicator member one revolution is equal to the number of teeth disposed about the periphery of the ratchet gear 552, 652. As the first indicator member is rotated by successive movements of the container relative to the housing, the advancement member 600, 800 of the first indicator member is brought into selective engagement with the engagement member, configured as the ramped surface 772 formed in the housing or as the upwardly extending arm member 700. In particular, the engagement member 700, 772 biases the tooth portion 604, 704 of the advancement member into engagement with one of the teeth 554, 654 of the ratchet gear on the second indicator member.

As the first indicator member is further rotated by successive movements of the container relative to the housing, whether it be the dispenser housing for the container or the module housing described below, the advancement member 600 engages one of the teeth on the ratchet wheel of the adjacent indicator member and advances the indicator member a predetermined incremental angular amount corresponding to the pitch of the ratchet gear teeth. The term incremental is meant to refer to the angular amount the indicator member is moved by the advancement of one actuation, which corresponds to the movement of one tooth, regardless of whether the indicating device is indicating the number of doses left (e.g., counting down) or indicating the number of doses administered (e.g., counting up).

As the resilient advancement member 600, 800 clears the engagement member 772, 700, it springs away from the ratchet gear such that further advancements of the first indicator member do not effect a rotation of the second indicator member until the first indicator member completes yet another cycle so as to again bring the advancement member into engagement with the next tooth of the second indicator member ratchet gear, and so on. The second indicator member 550, 650 with its advancement member 600, 800, similarly interacts with a second engagement member overlying the teeth of the third indicator member so as to selectively engage and advance the third indicator member a predetermined incremental amount for each complete rotation of the second indicator member. It should be understood that more indicator members could be similarly assembled to provide an incremental indicating device.

In a preferred embodiment of the dispensing device, shown in FIGS. 6-10, 13-18, 20, 24, 25 and 30, the indicator assembly is arranged in an indicator module 120, 1020, 1120. The indicator module 120, 1020, 1120 is shaped to be received within the housing where it is disposed around a portion of the support block 16. In particular, the support block is spaced apart from the wall of the dispenser housing, otherwise referred to as the actuator boot, so as to form a donut-shaped socket in the bottom of the housing. The module includes a module housing 130, 1030, 1130 having an inner concave surface 132, 1032, 1132 that is shaped to mate with an outer convex surface of the cylindrical support block and an outer convex 134, 1034, 1134 surface that is shaped to mate with the inner concave surface of the housing which is also generally cylindrical. In this way, the module housing is shaped to be received within the socket formed around the support block. Preferably, the module housing has a semicircular shape and fits around a portion of the support block opposite the orifice opening so as to not interfere with the dispensing of the medicament, or the airflow transmitting the medicament to the patient. In this way, the module is maintained rearwardly of the midpoint of the support block. One of sill in the art should understand, however, that the module, or module housing, can be configured in any number of different sizes and shapes so as to be accommodated in a variety of housings or cap assemblies, with or without support blocks and the like.

Figure 11:
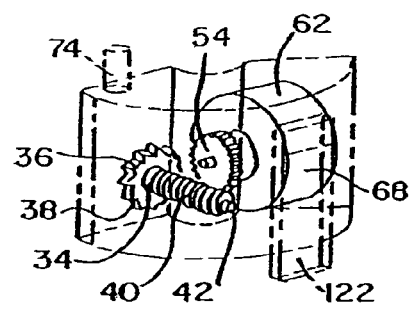
FIG. 11 is a perspective view of the alternative embodiment of the indicator module shown in FIG. 10.

As shown in FIGS. 8-9, one embodiment of the module preferably includes a face portion 210 that extends from the rear convex surface of the module and includes a module viewing window 64. The face portion snaps into the housing viewing window opening (circular opening not shown) so as to secure the module thereto. As shown in an alternative embodiment in FIGS. 10-12, the face portion includes a vertically oriented rectangular viewing window 68 and a downwardly extending locking member 122 which extends through the dispenser viewing window opening 124 and engages a bottom wall of the housing. In yet other embodiments, shown for example in FIGS. 24 and 30, the face portion 1031, 1131 and viewing window 1064, 1164 have an elongated horizontal orientation so as to provide the user with a view of the plurality of indicator members mounted within the module. It should be understood, however, that the module can be secured within the housing by any number of conventional means, including the use of fasteners or adhesive. Alternatively, the module can simply be press fit into the socket formed between the support block and housing wall.

In the embodiment shown in FIG. 8, the circular viewing window. 64 is provided in the module housing so as to expose a substantial portion of the planar indicator wheel. Numerical indicia, corresponding to the number of doses in the container, are provided on the face 80 of the indicator wheel. An arrow, or are indicator, is applied to the housing adjacent the viewing window and provides an indication of the number of doses remaining in the housing, or the number dispensed therefrom, as the indicator wheel is rotated.

In other alternative embodiments, shown for example in FIGS. 10, 11, 25 and 39, the indicia are applied to a circumferential surface 62, 660, 660 of the indicator wheel. The module viewing window 68, 1064, 1164, which is preferably rectangular, and indicator wheel are arranged such that the circumference, or periphery, of the wheel, or wheels, is visible through the module and dispenser viewing windows. As with the other embodiments, the indicia can take the form of color coding, shading, alpha-numerical characters and the like.

In the embodiments shown in FIGS. 28-29 and 42-43, the indicia are preferably formed around the circumferential surface 560, 660 of the indicator wheel in the form of numbers ranging from 0 to 9, with the ratchet gear on the indicator member having 10 teeth. In operation, it should be understood that the three, or more or less, indicator members can be preset to the maximum number of dosages contained within the container, with the indicia, or in this case numbers, arranged about the periphery of the indicator wheel, such that successive, sequential actuations of the container cause the indicator members to count down.

Alternatively, the indicator members are assembled such that the zero (0) of each indicator member is displayed in the viewing window to the user. The container is then actuated by the user such that the first indicator member rotates within the housing to sequentially display the number of doses that have been dispensed from 1 to 9. Upon the tenth actuation, the indicator member completes a single revolution, by virtue of the ten teeth preferably formed about the ratchet gear which correspond to the predetermined number of actuations, and causes the second indicator member to advance one number from 0 to 1 as the first indicator member again displays a 0 such that the two members together indicate that 10 dosages have been dispensed. The first indicator member is again rotated by successive actuations until another single rotation is completed to further rotate the second indicator to reveal the 2, so as to indicate that 20 dosages have been dispensed. Upon a complete rotation of the second indicator member, corresponding to 100 actuations, the third indicator member is advanced to reveal a 1 in the viewing window with the first and second indicator members revealing a 0, and so on.

Figure 30:
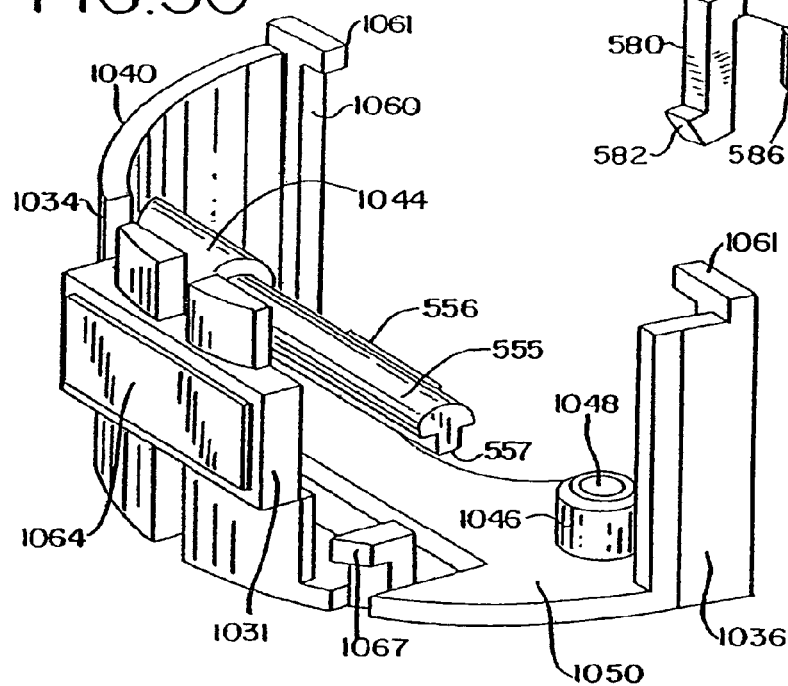
FIG. 30 is a top perspective view of a second member of one embodiment of the indicator module with an axle installed therein.
Figure 31:
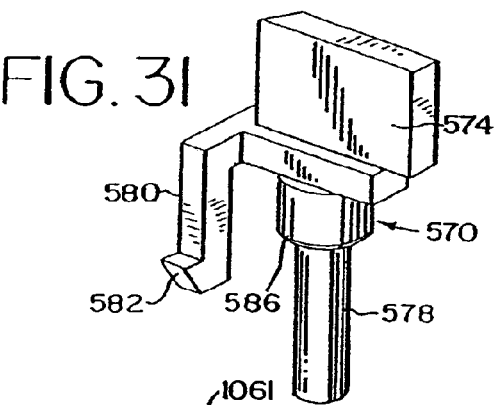
FIG. 31 is a perspective view of an actuator member.
Figure 35:
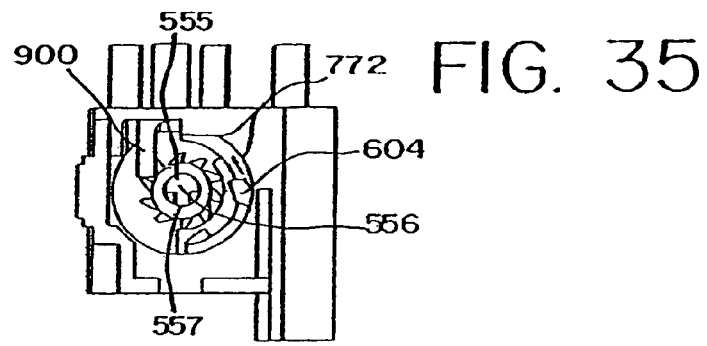
FIG. 35 is a cross-sectional view of an indicator module showing an advancement member of a first indicator member, an engagement member and a second indicator member.
Figure 36:
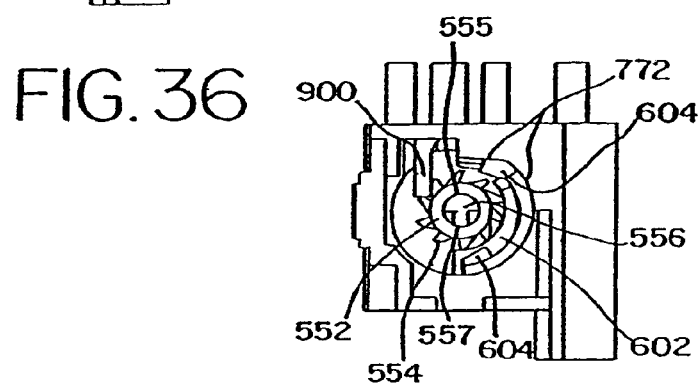
FIG. 36 is a cross-sectional view of the advancement member of the first indicator member as it is first engaged by the engagement member in the indicator module housing.
Figure 37:
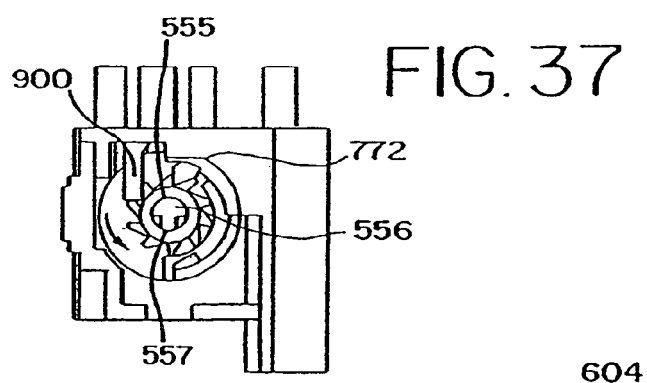
FIG. 37 is a cross-sectional view of the advancement member as it is biased by the engagement member into engagement with the second indicator member so as to rotate the second indicator member.
Figure 38:
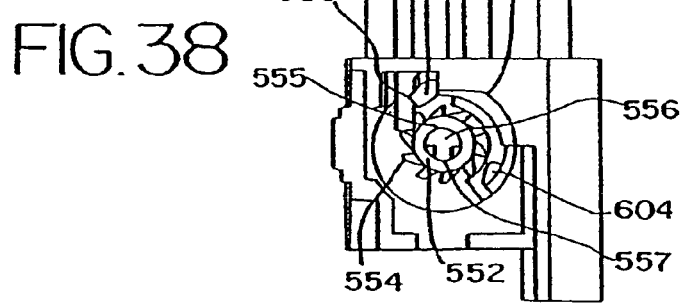
FIG. 38 is a cross-sectional-view of the advancement member as it is released by the engagement member and disengages from the second indicator member.

As shown in FIGS. 6-10, 13-18 and 20, one embodiment of the indicator assembly, including the worm, worm gear, ratchet gear and indicator member, is mounted within the module housing 130. Similarly, the embodiments of the indicator assembly shown in FIGS. 25 and 39 are also preferably supported in a module housing 1030, 1130. The module housing is preferably formed from a first and second cover member 136, 138, 1036, 1038, 1136, 1138 although it should be understood that a single, integral piece of material would also work, as would any plurality of members joined together. Referring to FIGS. 6-10, 30 and 39 the first cover member 136, 1136, 1036 has a vertical wall 140, 1140, 100 defining at least a portion of the outer convex surface 134, 1034, 1134 shaped to mate with the inner surface of the housing as described above. The secondary viewing window 64, 1064, 1164 of the module is provided in the vertical wall 140, 1040, 1140 so as to be aligned with the viewing window of the housing when the module is installed therein. The viewing window is framed by the face portion. In one embodiment, shown in FIG. 9, the first member also includes a pair of opposing bearing seats 144 formed on an inner surface of the vertical wall. The bearing seats 144 are shaped to support the ends of axle 42. Alternatively, as shown in FIGS. 27 and 30 a bearing seat or lug 1044 can be formed on each of the first and second cover members. As best shown in FIGS. 9 and 30, a post member 146, 104 extends upwardly from a base 150, 1050 of the first member adjacent one of the bearing seats and has a socket 148, 1048 formed coaxially therein. Alternatively, as best shown in FIG. 30, the base 1150 is formed as part of the second cover member and includes an opening 1148 shaped to receive the lower portion 678 of the actuator member.

Referring to FIGS. 8-9, the second cover member 138, 1038, 1138 males with the first cover 136, 1036, 1136 to form an enclosure therebetween. The second cover member includes a vertical wall 152, 1052, 1152, a portion of which defines the concave surface 132, 1032, 1132 shaped to mate with the outer surface of the support block. An upper horizontal flange 154, 1054, 1154 extends from the vertical wall 152, 1052, 1152 and mates with the vertical wall of the second member in overlying relationship therewith so as to close off the top of the module. In an alternate embodiment, the upper flange 1154 is formed as part of the first cover member. The upper flange 154, 1054, 1154 has an opening 156, 1056, 1156 formed therein which is shaped to receive the upper portion 74, 574, 674 of the post member. In one embodiment, the upper surface of the flange is maintained parallel with or below the top surface of the support block so as not to interfere with the container as it is depressed toward the support block. Alternatively, as shown in FIGS. 8 and 9, the module housing is provided with a semi-circular recess 155 shaped to receive the hub as the container is actuated whereby the surface 108 of the container engages the upper portion 74 of the actuator member and the Surface 108 is positioned adjacent to the surface 154 of the module housing when the valve is moved to the open position. A bottom edge 158 of the vertical wall mates with the base 150 of the first cover member to dose off the bottom of the module. As shown in FIGS. 8-9, 25-27 and 30, the cover members are joined by slidably engaging vertical flanges 160, 1060 on the first cover member with grooves 162, 1062 formed on the second cover member. Inwardly extending tabs 220, 1061 snap fit into slots 222, 1063 formed in the second cover member. In the embodiment shown in FIGS. 26, 27 and 30, a tab member 1067 engages opening 1071 formed in a wall member 1069 that further defines a portion of the outer concave surface of the module housing. Alternatively, it should be understood that the first and second cover members can be joined with fasteners, adhesive and the like.

As best shown in FIGS. 7, 15, 32 and 48, when the cover members are assembled to form the module housing, the upper portion 74, 574, 674 of the post member extends through the opening in the upper flange of the first cover member and engages the top surface 108 of the container, which is inverted in the housing. Alternatively, the actuator member can be attached to the hub of the container with the locking ring as previously described. In such an embodiment, the arm member of the actuator member extends downwardly from the ring through the opening in the top of the first cover member and is positioned to selectively engage the ratchet gear. The insertion of the arm in the opening prevents the canister and attached locking ring from being rotated so as to move the arm member out of position for selective engagement with the ratchet gear.

As best shown in FIGS. 9 and 25, the lower portion 78, 578 of the post member is moveably received within the socket 148, 1048 formed in the post member 146, 1040 extending from the base of the second cover member. Alternatively, the lower portion 678 is received in the opening 1148 as shown in FIG. 39. Referring to FIGS. 9, 25 and 39, spring 88, 588, 688 is disposed about the lower portion 78, 578, 78, and in certain embodiments includes a lower end mounted on the post member 146, 1046. The upper end of the spring engages the lower stop surface 86, 586, 686 of the post member 72, 572, 672. The spring biases the post member upwardly within the housing such that the upper portion 74, 674, 674 protrudes through the opening and into engagement with the top surface of the container 108.

In one embodiment, shown in FIGS. 8 and 9, the warm 40 and ratchet gear 32 are rotatably supported on the bearing seats 144 formed in the second member. Preferably, opposite ends of axle 42 are snap fitted into the bearing seats. The indicator member 50 is rotatably supported by the second cover member such that the worm gear engages the worm when the cover members are joined together. In particular, the second cover includes a pair of downwardly opening lug members 164, 166. The axle 56 of the indicator member is received in the first lug member 164 and a hub portion 69 positioned between the worm gear and the indicator wheel is received within the second lug member 166. Preferably, the axle and hub are snap fitted into the lugs, but are permitted to freely rotate therein. When the cover members are joined, the indicator member, and in particular the worm gear, are trapped between the lug members and the worm.

In an alternative embodiment shown in FIGS. 25-27 and 30, the axle 556 is supported on opposite ends by the lug portion 1044 extending from each of an upper and lower cover members 1036, 1038. The axle 556 has a T-shaped cross-section formed as a result of a molding process, e.g., when the axle is integrally formed or molded with one or more of the module housing cover members. The shape of the axle also permits it to act as a key member when received in similarly shaped sockets formed in one or more of the lug portions. The axle extends outwardly from the lug portion. The axle includes opposite curved surfaces 555, 567, as best shown in FIGS. 35-38 that provide a supporting surface for the indicator members that are rotatably mounted thereon. One of skill the art should understand that the axle could have a circular cross-section and could be rotatably mounted to the housing. In such an embodiment, at least one of the indicator members can be integrally formed with the axle, or all of the member can be separately mounted thereon.

It should be understood that in the alternative embodiment of FIGS. 2-5, the supporting structure for the worm end ratchet, including the bearing seats or like supports, and the supporting structure for the indicator member, including the lug members, are similar to the structure provided in the module housing, but are integrally molded into the housing. Similarly, a post and socket member can be integrally molded into the bottom of the dispenser housing so as to support the actuator member and spring.

Similarly, although the indicator assembly embodiments of FIGS. 25 and 39 are shown as preferably being mounted in the indicator module, one of skill in the art should understand that the assembly, including the axle, indicator members, actuator member and spring could be mounted directly in the dispenser housing or actuator boot that supports the container. Similarly, the engagement member, or members, and non-return member, or members, could be formed in the dispenser housing that supports the container, otherwise referred to as the actuator boot.

In an alternative embodiment shown in FIG. 19, a lower portion 172 of the outer vertical wall of the module housing is angled so as to a mate with a housing having a similar angled planar bottom surface. As shown in FIG. 19, the axis of rotation of the indicator member is oriented at an angle of approximately 45 degrees from the longitudinal axis so that the face of the indicator wheel 60 is substantially parallel to the angled surface of the housing. A viewing window is provided in the angled surface 172 and is aligned with a similar viewing window provided in the angled wall of the dispenser housing.

Now referring to FIGS. 21-23, a key member 300 is shown as including a base portion 302 having a recess 304 shaped to receive the top of the container. The base portion is circular shaped and is open in the middle. The key member is mounted on the container by press fitting a circumferential flange 306, which forms the recess, about the container such that the valve stem and hub passes though an opening 308 formed in the middle of the key member. Alternatively, the key member can be mounted to the container with adhesive or Other fasteners. The key member also includes a key portion 310 extending downwardly from the base portion. The key portion is preferably configured as a circular flange member, although other shapes would also work.

In alternative embodiments shown in FIGS. 25 and 32-33, the key member 1300 includes a mounting portion 1302, configured as a hoop member having a plurality of ribbed portions 1304. The mounting member 1302 is sized to fit over the end of the container such that the ribbed portions grip a portion of the container. A plurality of arm members 1306 secure a key portion 1308 to the mounting member.

In another alternative embodiment shown in FIG. 34, the mounting member 1402 has a smaller diameter than the key portion, and is coaxially disposed with the key portion. A base member 1404 connects the mounting member and key portion. The mounting member includes a plurality of inwardly facing tab members 1410 that engage an outer tapered surface of the hub portion 106 of the container.

In the embodiments shown in FIGS. 25 and 34, the key portion 1308, 1488 is formed as a circular flange member having a plurality of openings 1312, 1412 formed therein about the circumference thereof so as to allow air to flow through the key member with less restriction. In the embodiment shown in FIGS. 32 and 33, the key portion 1508 includes two coaxially mounted key portions of different diameters, each with a plurality of openings 1512 to facilitate air flow therethrough.

The embodiment of the indicator module shown in FIG. 21 has a key entry passageway configured as a recess 312 formed in an upper surface of the module housing. Preferably, in this embodiment, the recess is formed as an arcuate shaped, or semi-circular, slot. The actuator member 314 extends upwardly from the module housing into the slot. The actuator member 314 is maintained substantially flush with or below the upper surface of the module 316. In this way, the actuator cannot be actuated by a user's finger or the like so as to inadvertently advance the indicator member and thereby provide an inaccurate reading of the number of dosages remaining in the container, or the number dispensed therefrom.

The shape or diameter of the key portion and corresponding entry passageway are configured so that the key portion communicates with and is received in the passageway formed in the module housing. When the container is mounted in the dispenser housing such that the valve stem is received in the well in the support block, the key portion is received in the passageway and engages the actuator member.

In an alternative embodiment of the dispensing device, with or without an indicator module or indicator assembly, a key entry passageway can be formed directly in the dispenser housing, e.g., in a bottom portion of the dispenser housing, wherein it receives a key portion disposed on the container. It should be understood that the term "housing," as used herein, can refer to the dispenser housing, the indicator module housing, or a combination of those housings.

In yet another alternative embodiment, the key portion and key entry passageway are reversed. In this embodiment, the key portion is formed on the housing, i.e., the indicator module housing, or the dispenser housing if the dispensing device tacks an indicator module and/or an indicator assembly, and the key entry passageway is formed in the container. For example, the module housing, or dispenser housing, can include a ring member that is received in a ring-shaped recess formed in the hub of the container. Or, the dispenser housing or module housing can be configured to include one or more protuberances that are received in one or more recesses formed in the container.

In this way, key members having differently shaped key portions can be applied to containers holding different types of substances, such as a medicament, so as to prevent the user from mixing up the containers and dispensers. In operation, a container having a certain key member with a specific key portion can be installed only in a dispenser housing having a passageway shaped to receive that key portion. If the key portion does not fit the recess, the key ring will engage the upper surface of the module housing so as to prevent the actuation of the container relative to the dispenser housing end the attendant opening of the valve. This in turn prevents a user from installing containers having different substances in different dispenser, which could thereby adversely affect the counting of doses dispensed from the container, or the counting of the number of doses remaining therein. For example, a key member having a key portion with a thickness of 1 mm and an inner diameter of 13 mm is prevented from being installed in a passageway having a width of 1 mm and an inner diameter of 15 mm, and vice versa.

It should be understood that the mating key member and key entry passageway can also be used with various delivery systems that do not include an indicating device, as explained above. Often, delivery systems can be configured to deliver a specific type of substance. Because a differently configured delivery system may not maximize the delivery of the intended substance, such as a medicament, it may be important to ensure that a specific delivery system is used with a particular substance. In this way, a mating key member and key entry passageway can be mounted on one or the other of the container and housing, or similar structure, of the delivery system so as to ensure that the proper container is installed in the proper delivery system.

In the alternative embodiment of FIG. 25, the module housing includes three pairs of upstanding members 1080, 1082 forming a slot or recess 1084 between each pair. In addition, the upstanding members of one pair 1082 are formed as channels opening towards each other. The elongated recess 1056 formed between the pair of members is shaped to receive the upper portion of the actuator member 574. In operation, the key portion 1308 of the key member is shaped to be received in the various radially formed slots or recesses, or key entry passageways, so as to engage the actuator member disposed in the elongated recess. When the container is moved with respect to the module housing so as to move the valve to the open position, the hub of the container nests in a recess formed between the inner upstanding member of each pair.

In the embodiment shown in FIGS. 32 and 33, three sets of three upstanding members 1180, 1182 are provided, with each set of three having two slots 1184 formed between the members so as to be shaped to receive the two key portions 1508 of the key member 1500. Again, one set of three members 1182 forms an elongated passageway, or recess 1056, that is shaped to receive the actuator member. The two key portion configuration allows for multiple combinations of shapes and diameters of key portions so as to provide for a different key combination for each of the multiplicity of substances being dispensed from the various containers.

Although the circular configurations of the key portion and corresponding slots shaped to receive the key portion, as shown in the figures, are preferred since they allow the container to be rotated within the dispenser housing about its longitudinal axis, it should be understood that the key portion and slot, or like passageway or keyhole, can be shaped in any type of mating configuration and that the mating shapes are not limited to the circular configuration shown in the figures.

The indicator module provides an inexpensive and accurate device for counting dosages of medicament and the like. The module can be sized for easy installation as a separate unit in most conventional inhalation housings with minimal modification of the housing, including providing a viewing window in the housing in alignment with the module viewing window and the removal of any structure formed between the support block and outer wall of the housing. In addition, the module can be installed rearwardly of the support block, so as not to interfere with or otherwise impede the air low dispensing the medicament.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A dispensing device for dispensing metered dosages of a medicament from a container, the dispensing device comprising:
    a dispenser housing having an interior surface defining a cavity, said dispenser housing comprising a support block having a well, said support block defining a longitudinal axis and having an outer surface;
    an indicator housing comprising a first cover comprising a first vertical wall disposed adjacent said interior surface of said dispenser housing and a second cover comprising a second vertical wall disposed adjacent said outer surface of said support block, wherein one of the first or second covers comprises a base defining a lower surface of said indicator housing, and the other of the first or second covers comprises a top defining an upper surface of said indicator housing, wherein said first and second covers are joined with said first and second vertical walls and said base and said top defining an interior space therebetween; and
    an indicator rotatably disposed in said interior space of said indicator housing, said indicator comprising dosage indicia.

2. The dispensing device of claim 1 further comprising said container having a valve stem disposed in said well, wherein said container holds a medicament.

3. The dispensing device of claim 1 wherein said first vertical wall comprises an outer convex surface.

4. The dispensing device of claim 3 wherein said second vertical wall comprises an outer concave surface.

5. The dispensing device of claim 4 wherein said outer concave surface mates with said outer surface of said support block.

6. The dispensing device of claim 1 wherein said first and second cover members are joined with a snap fit.

7. The dispensing device of claim 1 wherein said first vertical wall comprises a first viewing window, wherein said dosage indicia of said indicator are visible through said first viewing window.

8. The dispensing device of claim 7 wherein said dispenser housing comprises a second viewing window aligned with said first viewing window, wherein said dosage indicia of said indicator are visible through said second viewing window.

9. The dispensing device of claim 1 wherein said indicator is coupled to at least one of said first and second covers with a snap fit.

10. An indicating device for a dispenser that dispenses metered dosages of a medicament from a container having a valve moveable between a closed position and an open position, said indicating device comprising:
    an indicator housing comprising a first cover comprising a first vertical wall and a second cover comprising a second vertical wall, wherein one of the first or second covers comprises a base defining a lower surface of said indicator housing, and the other of the first or second covers comprises a top defining an upper surface of said indicator housing, wherein said first and second covers are joined with said first and second vertical walls and said base and said top defining an interior space therebetween; and
    an indicator rotatably disposed in said interior space of said indicator housing between said first and second vertical walls, said indicator comprising dosage indicia.

11. The indicating device of claim 10 wherein said first vertical wall comprises an outer convex surface.

12. The indicating device of claim 11 wherein said second vertical wall comprises an outer concave surface.

13. The indicating device of claim 10 wherein said first and second cover members are joined with a snap fit.

14. The indicating device of claim 10 wherein said first vertical wall comprises a first viewing window, wherein said dosage indicia of said indicator are visible through said first viewing window.

15. The indicating device of claim 10 wherein said indicator is coupled to at least one of said first and second covers with a snap fit.

* * * * *